(12) United States Patent
    Pettersson

(10) Patent No.: US 10,810,282 B2
(45) Date of Patent: Oct. 20, 2020

(54) COMPUTER IMPLEMENTED PLANNING AND PROVIDING OF MASS CUSTOMIZED BONE STRUCTURE

(71) Applicant: NOBEL BIOCARE SERVICES AG, Kloten (CH)

(72) Inventor: Andreas Pettersson, Gothenburg (SE)

(73) Assignee: Nobel Biocare Services AG, Kloten (CH)

( * ) Notice: Subject to any disclaimer, the term of this patent is extended or adjusted under 35 U.S.C. 154(b) by 792 days.

(21) Appl. No.: 15/620,469

(22) Filed: Jun. 12, 2017

(65) Prior Publication Data

US 2017/0344720 A1    Nov. 30, 2017

Related U.S. Application Data

(63) Continuation of application No. 12/682,614, filed as application No. PCT/EP2008/008553 on Oct. 10, 2008, now abandoned.

(51) Int. Cl.
    *G06F 19/00*    (2018.01)
    *G06Q 50/22*    (2018.01)
    *G16H 50/50*    (2018.01)

(52) U.S. Cl.
    CPC ............ *G06F 19/00* (2013.01); *G06F 19/321* (2013.01); *G06Q 50/22* (2013.01); *G16H 50/50* (2018.01)

(58) Field of Classification Search
    CPC ....... G06F 19/00; G06F 19/321; G06Q 50/22; G16H 50/05

(Continued)

(56) References Cited

U.S. PATENT DOCUMENTS 5,816,810 A    10/1998 Antonson et al.
5,851,115 A    12/1998 Carlsson et al.
(Continued)

FOREIGN PATENT DOCUMENTS

EP    1568335    8/2005
EP    1571581    9/2005
(Continued)

OTHER PUBLICATIONS

Michael Meehan et al., Virtual 3D Planning and Guidance of Mandibular Distraction Osteogenesis, Comput Aided Surg. (Mar. 2006);11(2), 51-62.

(Continued)

*Primary Examiner* — Joy Chng
(74) *Attorney, Agent, or Firm* — Knobbe, Martens, Olson & Bear, LLP

(57) ABSTRACT

A computer-implemented method, a system and a computer program is disclosed, which comprise virtual planning of a medical procedure of a patient. The medical procedure comprises providing a patient configured bone structure in a body portion of the patient. Based on an input of a final result of the medical procedure, the bone structure may be modified by various tools and methods, such a bone implants, bone distractive methods, etc. Production data based on the virtual planning is generated that is configured for subsequent use in production of the bone structure or a medical product, which medical product is devised for use in the medical procedure, and devised for arrangement in the patient for facilitating the medical procedure. The virtual planning of a medical procedure comprises providing position data for a position of at least a part of a prosthesis component in relation to the body portion, and virtual planning of a modification of a boundary surface at the body portion as a function of the position data.

17 Claims, 17 Drawing Sheets

(58) Field of Classification Search
USPC .......................................................... 705/2–3
See application file for complete search history.

(56) References Cited

U.S. PATENT DOCUMENTS

| | | | |
|---|---|---|---|
| 6,814,575 B2 | 11/2004 | Poirier | |
| 7,942,668 B2 | 5/2011 | Brajnovic et al. | |
| 8,186,999 B2 | 5/2012 | Andersson et al. | |
| 2002/0059049 A1 | 5/2002 | Bradbury et al. | |
| 2004/0171924 A1* | 9/2004 | Mire ...................... | A61B 34/20 600/407 |
| 2005/0089822 A1* | 4/2005 | Geng ...................... | G06F 30/00 433/215 |
| 2007/0077551 A1* | 4/2007 | Hirayama ........ | G01N 35/00584 435/4 |
| 2007/0118243 A1* | 5/2007 | Schroeder .......... | A61B 17/8061 700/118 |
| 2007/0190492 A1* | 8/2007 | Schmitt .............. | A61C 13/0004 433/213 |
| 2008/0262624 A1* | 10/2008 | White .................. | A61F 2/3836 623/20.32 |
| 2009/0325122 A1 | 12/2009 | Brajnovic et al. | |
| 2010/0028827 A1 | 2/2010 | Andersson et al. | |
| 2010/0332248 A1 | 12/2010 | Pettersson | |
| 2011/0008751 A1 | 1/2011 | Pettersson | |
| 2011/0060558 A1 | 3/2011 | Pettersson et al. | |
| 2012/0123576 A1 | 5/2012 | Pettersson et al. | |

FOREIGN PATENT DOCUMENTS

| | | |
|---|---|---|
| WO | WO 01/15058 | 3/2001 |
| WO | WO 2004/110309 | 12/2004 |
| WO | WO 2007/045000 | 4/2007 |

OTHER PUBLICATIONS

International Search Report for International Application No. PCT/EP2008/008553 dated Feb. 2, 2009.

* cited by examiner though Swedish Patent Application No. 0702304-7, filed Oct. 12,

COMPUTER IMPLEMENTED PLANNING AND PROVIDING OF MASS CUSTOMIZED BONE STRUCTURE

CROSS-REFERENCE TO RELATED APPLICATIONS

This application is a continuation of U.S. patent application Ser. No. 12/682,614, filed Sep. 14, 2010, which is a national stage application under 35 U.S.C. § 371 of PCT Application No. PCT/EP2008/008553 designating the United States, filed on Oct. 10, 2008. The PCT Application was published in English as WO 2009/046987 A1 on Apr. 16, 2009, and claims the benefit of the earlier filing date of Swedish Patent Application No. 0702304-7, filed Oct. 12, 2007. The contents of PCT Application No. PCT/EP2008/008553 is incorporated herein by reference in its entirety.

BACKGROUND

Field of the Invention

This invention pertains in general to the field of medical procedures. More particularly the invention relates to computer implemented virtual planning of medical procedures involving skeletal adjustments.

Description of the Related Art

In WO07045000 methods, techniques, materials and devices and uses thereof are disclosed for custom-fitting biocompatible implants, prosthetics, and interventional tools for use on medical applications. The devices produced according to the disclosure of WO07045000 are created using additive manufacturing techniques based on a computer generated model such that every prosthesis or interventional device is personalized for the user having the appropriate metallic alloy composition and virtual validation of functional design for each use.

However, the disclosure of WO07045000 allows only additive adjustments of a prosthesis to an existing skeletal situation, which is a serious limitation concerning the medical procedures that may be implemented.

Distraction osteogenesis is a surgical process used for the reconstruction of skeletal deformities. The bone is surgically (with a corticotomy) split in two segments. Distraction technology has been used mainly in the field of orthopedics, but the process has shown equally effective in facial skeletal reconstruction.

However, planning of such distraction surgical processes is hitherto based on a trial and error principle, or very much dependent on the experience of the surgeon performing the distraction process. The final result thus may vary substantially from the result that initially was planned.

Hence, an improved method, system, and/or computer program comprising virtual planning of a medical procedure involving adjustment of a bone structure of a patient would be advantageous, in particular allowing for increased flexibility, cost-effectiveness, reliability, patient safety, and/or patient satisfaction would be advantageous.

SUMMARY

Accordingly, embodiments of the present invention preferably seeks to mitigate, alleviate or eliminate one or more deficiencies, disadvantages or issues in the art, such as the above-identified, singly or in any combination by providing a method, a system, a computer program, a medical workstation, and a graphical user interface according to the appended patent claims.

According to a first aspect of the invention, a method is provided, wherein the method is a computer-implemented method. The method comprises virtual planning of a medical procedure of a patient, which medical procedure comprises providing a patient configured bone structure in a body portion of the patient. Furthermore, the method comprises in some embodiments generating production data based on the virtual planning, wherein the production data is configured for subsequent use in production of the bone structure or a medical product, which medical product is devised for use in the medical procedure, and devised for arrangement in the patient for facilitating the medical procedure. The virtual planning of a medical procedure comprises providing position data for a position of at least a part of a prosthesis component in relation to the body portion, and virtual planning of a modification of a boundary surface at the body portion as a function of the position data.

According to a second aspect of the invention, a system is provided. The system is devised for computer-implemented virtual planning of a medical procedure of a patient, which medical procedure comprises providing a patient configured bone structure in a body portion of the patient. In some embodiments, the system comprises a unit for generating production data based on the virtual planning, wherein the production data is configured for subsequent use in production of the bone structure or a medical product, which medical product is devised for use in the medical procedure, and devised for arrangement in the patient for facilitating the medical procedure. The system for virtual planning of a medical procedure comprises a unit for providing position data for a position of at least a part of a prosthesis component in relation to the body portion. Furthermore, the system comprises a unit for virtual planning of a modification of a boundary surface at the body portion as a function of the position data.

According to a further aspect of the invention, a computer program for processing by a computer is provided. The computer program comprises a first code segment for virtual planning of a medical procedure of a patient, which medical procedure comprises providing a patient configured bone structure in a body portion of the patient. In some embodiments, a second code segment for generating production data based on the virtual planning is provided, wherein the production data is configured for subsequent use in production of the bone structure or a medical product, which medical product is devised for use in the medical procedure, and devised for arrangement in the patient for facilitating the medical procedure; a third code segment for providing position data for a position of at least a part of a prosthesis component in relation to the body portion, and a fourth code segment for virtual planning of a modification of a boundary surface at the body portion as a function of the position data are provided.

Further embodiments of the invention are defined in the dependent claims, wherein features for the second and subsequent aspects of the invention are as for the first aspect mutatis mutandis.

Some embodiments of the invention provide for creation of an aesthetically sound body portion of a patient.

Some embodiments of the invention provide for re-creation of an anatomically previously existing structure.

Some embodiments of the invention provide for creation of a more anatomically correct body portion of a patient.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1A:
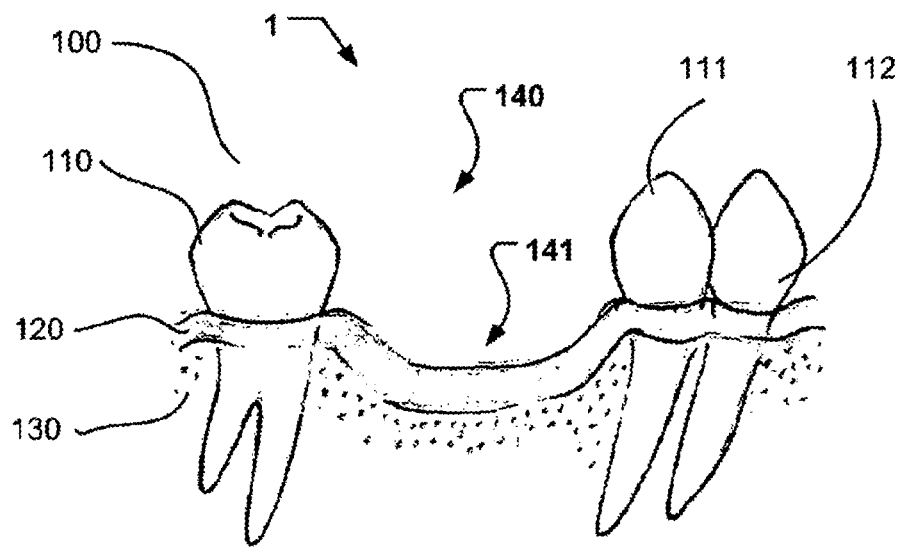
FIGS. 1a to 1g are illustrations of a computer based method of virtually planning a medical procedure, namely of a body portion with insufficient bone structure for a desired aesthetical creation and creation of a sufficient structure by means of a medical implant.

Specific embodiments of the invention now will be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Figure 5:
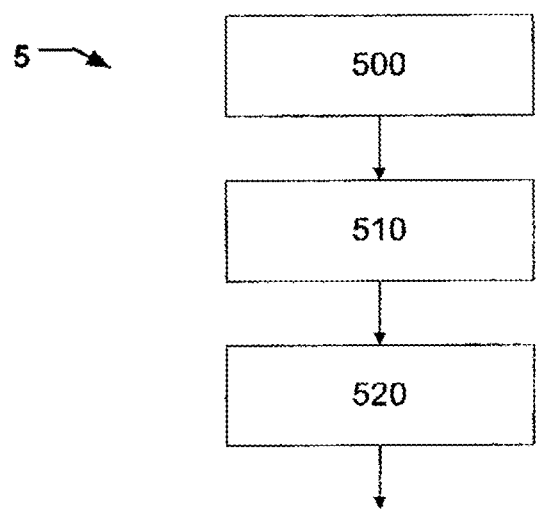
FIG. 5 is a flowchart of an embodiment of a method of virtually planning a medical procedure.

In embodiments a tool for virtually planning a medical procedure, e.g. a dental restorative procedure, is provided. FIG. 5 is a flowchart of an embodiment of a method 5 of virtually planning a medical procedure.

A final, or at least planned final, outcome of the medical procedure is provided in step 500, e.g. by virtual planning methods based on patient input data. From this initial point, i.e. the final outcome, a skeletal situation of the patient is analyzed in step 510. A desired bone structure is virtually planned in order to achieve the previously planned final outcome in step 520. Various tools for providing the bone structure may be used for the virtual planning of the bone structure, such as controlling bone growth and bone ingrowth, providing bone prosthesis, removing of bone portions, etc. Data is provided from the virtual planning for subsequent production of the bone structure or a medical product, which medical product is devised for use in the medical procedure, and devised for arrangement in the patient for facilitating the medical procedure.

In embodiments the virtual planning is provided as a computer-implemented method comprising the virtual planning of the medical procedure of the patient, wherein the medical procedure comprises providing a patient configured bone structure in a body portion of the patient. Data based on the virtual planning is generated, wherein the data is configured for subsequent use in production of the bone structure or the medical product. A real medical procedure may thus be performed based on the virtual planning.

The following description focuses on embodiments of the present invention applicable to virtual planning and subsequent creation of an oral or a maxillofacial bone structure. However, it will be appreciated that the present invention is not limited to this application but may be applied to many other anatomical structures, including for example structures of the skull, such as eyes, ears, noses, chins, etc. The medical procedure may comprise dental surgery, such as maxillofacial surgery, orthognathic surgery, and/or cosmetic surgery.

Starting Point

In embodiments a computer implemented virtual planning of the final outcome of a medical procedure for providing a body portion in a desired form, shape, appearance, look, etc. is provided. For instance, in orthognathic surgery, the final outcome is a proper occlusion, i.e. the manner in which teeth and molars of the upper and lower jaw fit on each other, and an aesthetically pleasing face.

This virtual planning of the final outcome of the medical procedure may comprise:

Virtual planning of a dental restoration, e.g. comprising positioning of dental implants bearing a bridge construction.

Taking into consideration treatment parameters, such as occlusion line, bite index, lip position, and/or good aesthetics, for defining an acceptable final outcome of the medical procedure.

Emanating from this virtually planned final result, the bone structure at a body portion of the patient is analyzed with reference to the final result. This analysis may result in a need of changing the existing anatomical skeletal structure at the body portion of the patient in order to be able to achieve the final result with the medical procedure.

The bone structure may have to be added with additional material, for instance to provide a structure for keeping implants in place, holding a bridge structure or other dental restoration. In this case, the anatomical structure at the body portion may be provided with an artificial element, such as a bone prosthesis or bone implant. Alternatively, or in addition, bone replacement material may be provided at the body portion to provide the desired bone structure facilitating achieving the planned final result of the medical procedure. Alternatively, or in addition, an autograft bone substitute of the same patient may be virtually planned. For instance, data provided from the virtual planning may be used for producing a suitable cutting template for harvesting bone. Alternatively, or in addition, bone growth may be simulated in a suitable way to provide a desired bone structure, such as for instance by using suitable bone growth substances, such as hydroxyapatite. Alternatively, or in addition, suitable bone creating medical procedures may be added to the virtual planning of the medical procedure, such as distraction techniques.

Alternatively, or in addition, it may be necessary to remove a portion of bone at the body portion in order to be able to achieve the desired final result of the medical procedure.

Cutting templates may be used for removing at least part of a bone structure that is hindering to achieve the desired final result, e.g. for providing a good aesthetical result. This may be the case if a position of a prosthesis collides with existing bone tissue in order to achieve a desired aesthetic final result. It may for instance be necessary to remove a part of jaw tissue to get access to a bone region suitable for insertion of a dental implant that later carries a dental restoration in order to achieve e.g. a good lip position, occlusion, bite index, and/or smile, etc. In addition, or alternatively, a bone structure may be adapted by removing bone therefrom in order to increase mechanical strength of an implant in bone tissue.

In some embodiments, a cutting template is provided for giving a surgeon a guidance where to cut a bone structure. A cutting template may for instance be used for harvesting bone or for cutting bone in a suitable way for a distraction procedure. Alternatively, or in addition, a cutting template may be used for removing bone from the body portion where the medical procedure for achieving the desired final result is performed, in order to provide a desired bone structure.

In some embodiments, the desired final result of a medical procedure may be provided before planning or starting the procedure itself. For instance, in patients suffering from bone cancer in a body portion, at least the bone struck with cancer has to be surgically removed. The aesthetical appearance and the bone structure may be registered before the surgical bone removal procedure. Patient data based on this input may be used as the final result of the subsequent medical recreation procedure. After having removed the bone portion as necessary by the medical indication, patient data of this anatomical situation may be provided by suitable means, as described further below.

In this manner, a single medical procedure session may comprise providing a bone structure, e.g. by removing bone tissue material by means of a cutting template, and attaching a pre-planned and pre-manufactured prosthesis in relation to the body portion having a bone structure that is adapted to provide a desired final result of the medical procedure.

Some specific embodiments illustrating such virtual planning of medical procedures, and subsequent steps, are given further below.

Indata

Indata for the computer based virtual planning of a medical procedure may comprise digitized patient data, including:

3D data—provided from scanning an impression or a cast model of a body portion of the patient, e.g. using touch probe scanners or optical scanners.

Patient data from imaging modalities, such as CT, MR, X-ray, Ultrasound.

2D and 3D photographies.

3D skeletal and/or skin models.

From the digitized patient indata a diagnosis and the virtual treatment planning may be performed. This patient treatment planning allows for a design and product customization of products to be used in the medical procedure. In this manner data is provided for production of such medical products, such as implants, prosthesis, membranes for casting bone replacement material, surgical templates, cutting templates, surgical templates for drill and implant guided surgery, guiding templates for distraction procedures, etc. Products may comprise provisional bridges, frameworks for bridges, final bridges, copings, abutments, surgical templates, bone prosthesis, 3D bone anatomical implants, membranes, etc.

Based on this data, the products may be produced and used for performing a real medical procedure based on the virtual planning thereof.

Planning Tools

In order to virtually plan a desired final result of a medical procedure, several tools may be used, such as for instance a library of virtual teeth; an image of a body portion, such as a face; a virtual articulator such as described in WO95/22299 of the same applicant as the present application, which is incorporated herein by reference in its entirety; simulations of implant positions for providing data for a surgical template for drill and implant guided surgery, or a cutting template; etc. By means of such tools a desired final result of a medical procedure may be virtually determined or verified.

Matching of several CT scans may be made according to the Dual Scan technique provided by the NobelGuide® concept. It is for example used for matching a radiographic guide with patient data.

Another matching technique for matching data from different input sources is for instance described in patent application PCT/EP2007/050426, filed on Jan. 17, 2007, of the same applicant as the present application, which is incorporated herein by reference in its entirety.

In summary, a present anatomical situation of the patient, is known, e.g. based on patient input data, e.g. from imaging modalities, such as CT, MR, or impressions of body portions of the patient that are scanned. The final result of a medical procedure is virtually planned, and may for instance be presented on a display of a medical workstation. Then an adaptation of the bone structure for achieving the final result is determined by the virtual planning. The virtual planning may provide data to be used for producing medical products used in the medical procedure. In this manner, a real medical procedure may be performed based on the virtual planning thereof. During the real medical procedure the medical products may be used, which are produced based on the data of the virtual planning and or the input data.

Embodiments

FIGS. 1a to 1g are illustrations of a computer based method of virtually planning a medical procedure, namely of a body portion with insufficient bone structure for a desired aesthetical creation and creation of a sufficient structure by means of a medical implant.

In FIG. 1a a schematic illustration 100 of an anatomical situation of a body region 1 of a patient is given. More precisely, a schematical illustration of a portion of the oral cavity of the patient is illustrated. Patient data on which the illustration may be based may for instance be acquired by suitable units, as described above in the section "Indata". The portion of the oral cavity illustrated comprises a tooth gap 140 between a first tooth 110 and a second tooth 111. A third tooth 112 is illustrated adjacent to the second tooth 111. The teeth are rooted in jaw bone tissue 130 which is covered by soft tissue 120. Bone tissue 130 in the edentate tooth gap 140 has regressed, leaving a recession of the bone crest in the region of the tooth gap 140. In case dental implants were installed in the tooth gap 140, an aesthetical or practically functional creation of a dental restoration would not be possible. In order to create a good occlusion, the top of a dental restoration has basically to be on the same level as that of the still remaining teeth. However, in this case a portion of each implant and the gap between these would be visible, which is aesthetically undesirable, and/or which provides insufficient stability of the implant. On the other hand, by using shorter dental implants, a desired occlusion cannot be achieved with natural looking, proportionally correct dental restorative teeth.

Figure 1B:
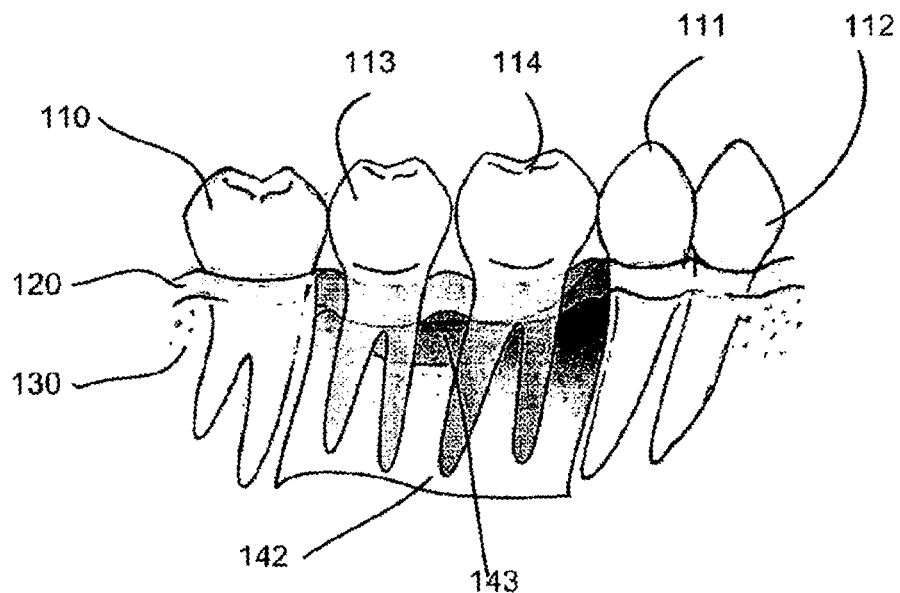

In FIG. 1b a desired final result of virtually planning a dental restorative procedure is illustrated, however still with the bone tissue 130 recessed at the tooth gap 140. In more detail, two library teeth 113, 114 are virtually positioned in order to achieve a good aesthetical result and occlusion line. In the region of the tooth gap 140 the desired extension of soft tissue 120 and bone tissue 130 is also illustrated. As can be seen, an interspace 143 has to be filled in a suitable way in order to lift the bone crest at the tooth gap 140 to a suitable level, in order to achieve the desired final result of the dental restorative procedure.

By means of a computer-implemented method a virtual planning of a medical procedure to achieve the desired final result is used. The medical procedure provides a patient configured bone structure in the body portion of tooth gap 140. Based on this virtual planning, production data is generated which is configured for subsequent use in production of the bone structure or a medical product, which medical product is devised for use in the medical procedure, and devised for arrangement in the patient for facilitating the medical procedure. The virtual planning of the medical procedure comprises providing position data for a position of at least a part of a prosthesis component in relation to the body portion, here the upper surface, or occlusion surface, of the virtual library teeth 113, 114. Further, the method comprises virtual planning of a modification of a boundary surface at the body portion as a function of the position data, here the boundary surface of the jaw bone tissue 130 in the tooth gap 140 is moved from the recessed position to a leveled position in line with the remaining crest of the jaw bone tissue 130. This method will now be described in further detail.

Figure 1C:
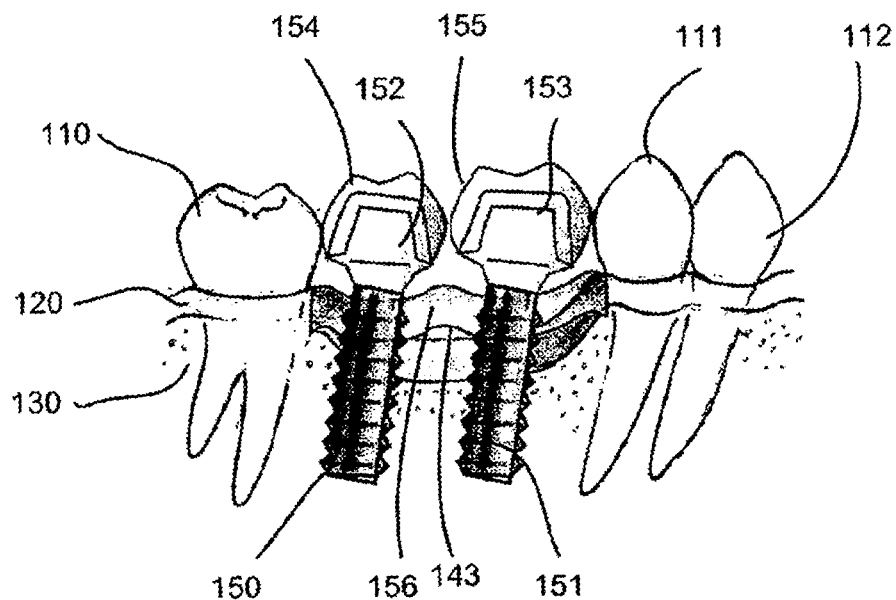

In FIG. 1c, a virtual planned final result of the dental restorative procedure is illustrated with two dental implants 150, 151, comprising threaded portions inserted into the bone tissue 130 and the interspace 143, as well as a corrected portion 156 of soft tissue 120. The boundary surface is desired to be lift up, as illustrated in FIG. 1c. The two dental implants 150, 151 have dental crowns 154, 154 attached at their apical part via suitable abutments 152, 153. The virtual transition from the virtual library teeth 113, 114 to the virtually planned dental implants 150, 151 having dental crowns 154, 154 may be done automatically by means of suitable algorithms, or semi automatically including manual correction of a suggested transition, or completely manually by choosing suitable dental implants from a range of standard sizes and planning of the dental crowns in accordance with the position of the top portion of the library teeth. This virtually planned rehabilitation may be made in a dental planning software, such as Procera® of Nobel Biocare, having a suitable plug in or software routine for virtually planning a bone structure adaptation to a desired final result of a dental restorative procedure.

Figure 1D:
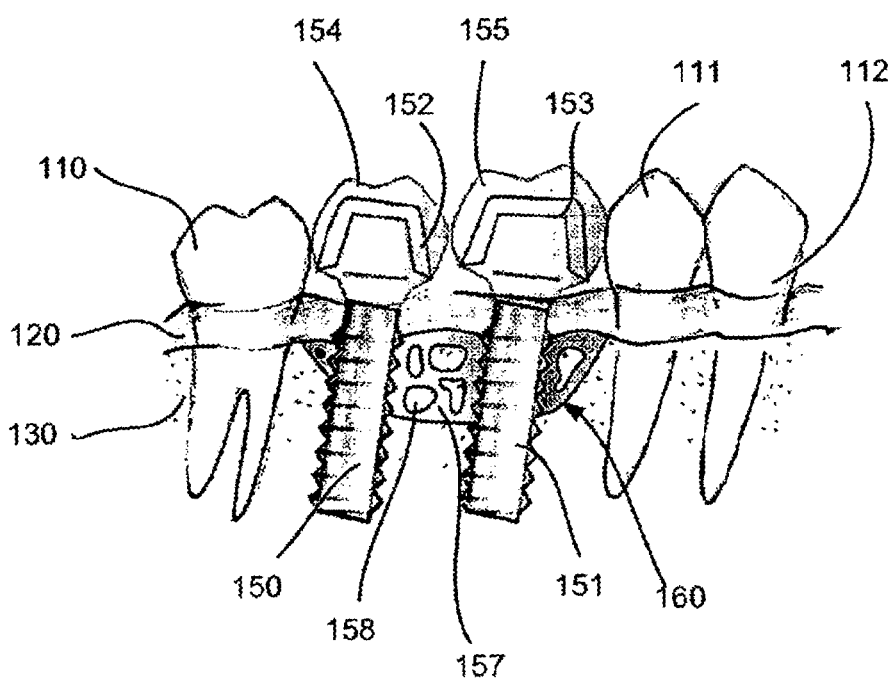

The lifting up of the boundary surface is in this embodiment achieved by providing a bone filling of the recess 141, as illustrated in FIG. 1d. The creation of structures to fill the interspace 143 and thus to modify the boundary surface may be done in many different ways. Two examples are described below with reference to FIGS. 1d to 1g, and FIGS. 2a to 2i, namely providing a bone replacement implant or creating a bone substitute by means of a membrane technique. In FIGS. 3a to 3g modification of the boundary surface is achieved by removal of bone tissue. In some embodiments different boundary modification may be used in combination to provide a desired final outcome of a medical procedure. Combinations of the embodiments may also be used.

Figure 1E:
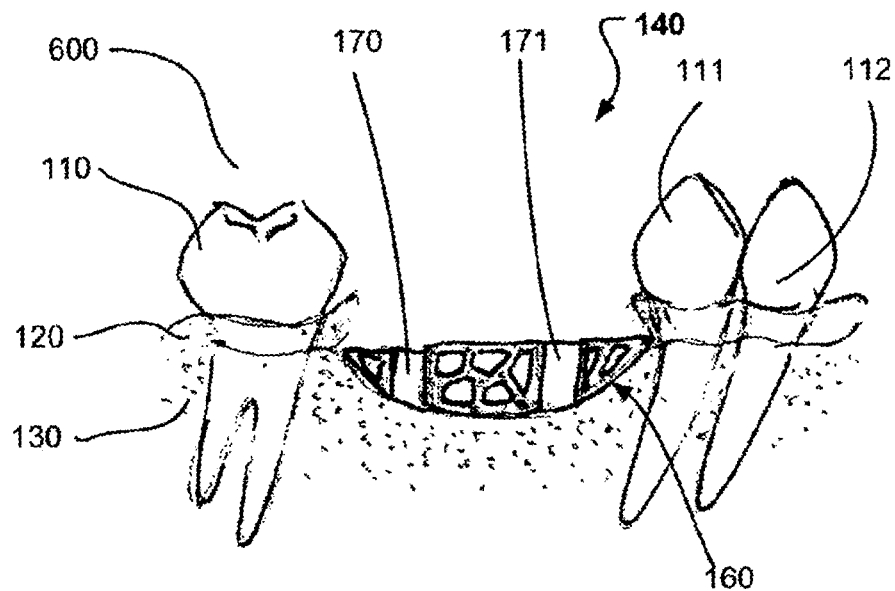

In FIGS. 1d to 1e, a bone implant 160 is virtually planned and the final result of a dental restorative procedure is shown that fulfill requirements with regard to e.g. aesthetics, stability and strength. From the virtual planning, data may be provided for producing the bone implant 160. The bone implant may be made from various materials and in different techniques, e.g. solid Free Form Fabrication, as explained below. The bone implant 160 may comprise a suitable material 157 and a reinforcing material and/or a osseopromoting agent or structure 158, such as hydroxyapatite (HA) or Tiunite® or Ziunite®. The bone implant 160 comprises suitable bushings 170, 171 for receiving the dental implants.

Figure 1F:
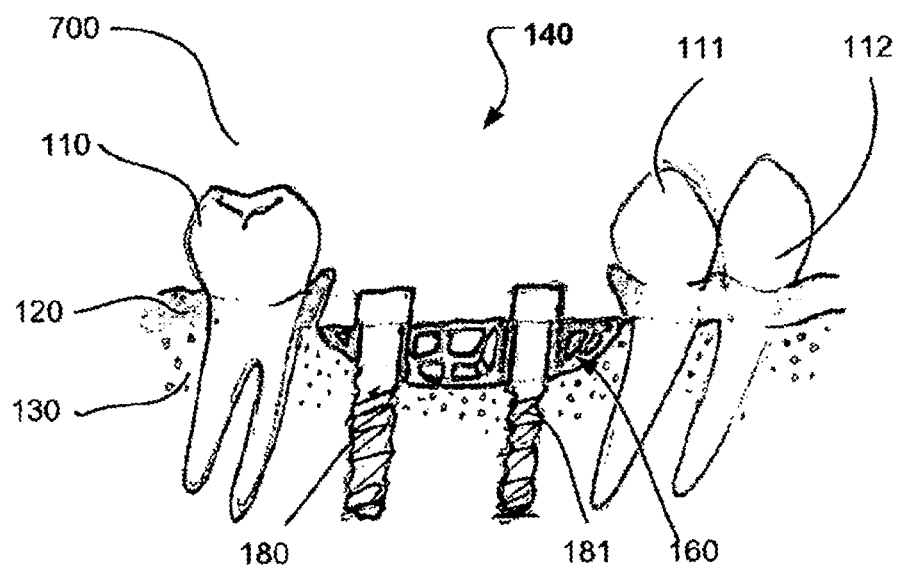

FIGS. 1e to 1f illustrate how the bone implant 160 is installed in the tooth gap 140 during a medical procedure. The bone implant may be fixed to the bone tissue 130, e.g. by means of bone cement or an osseoconductive surface that integrates the bone implant 160 with bone tissue 130 at the position of the tooth gap 140. In this case, a surgical template for drill and implant guided surgery with guide sleeves for controlled steering of drills for drilling holes for the dental implants may not be necessary, which means a step less has to be performed by the dental surgeon performing the dental restorative procedure. The bone implant 160 fulfills thus a second function, namely to provide a guide for a drill in a desired direction and to provide a stop for the drill, thus enabling providing of a hole for receiving a dental implant in a well defined direction and depth in bone tissue 130 and bone implant 160. However, a separate surgical template for drill and implant guided surgery may be used for positioning dental implants.

Alternatively or in addition, a surgical template for drill and implant guided surgery may be used for drilling holes in the bone tissue 130 and/or bone implant 160, wherein the dental implants 180, 181 optionally may keep the bone implant in place by a suitable design, such as head having a shoulder abutting against the bone implant, as shown in FIG. 1f.

The bone implant 160 may comprise and integral connection interface for attaching dental prosthetic components to the latter. The connection interface may for instance comprise a hexagonal protrusion, a recess, with an internal at least partly hexagonal shape, or multiple lobes, such as connection interfaces comprised in the commercially available products NobelReplace™ or the Branemark® system of the applicant of the present application. The connection interfaces provide at least a rotational locking of the prosthetic components.

Figure 1G:
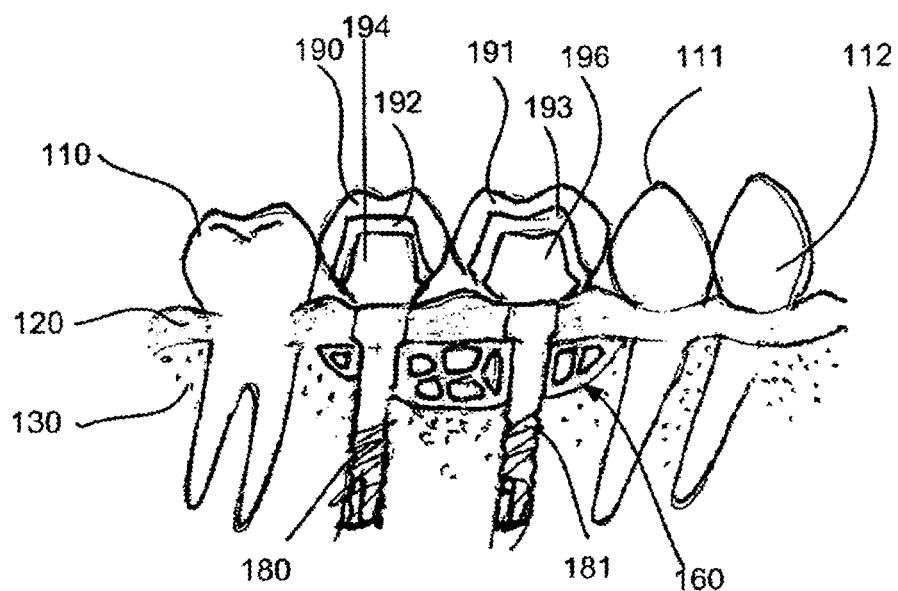

In FIG. 1g the final result of the dental restoration is illustrated, wherein crowns 190, 191 are attached to the dental implants via suitable abutments 195, 196 and by means of a suitable adhesive 192, 193 or other fixation means, such as press fitting.

FIGS. 2a to 2i are illustrations of a computer based method of virtually planning a medical procedure, namely of a body portion with insufficient bone structure for a desired aesthetical creation and creation of a sufficient structure by means of a membrane treatment creating an artificial bone structure.

Figure 2A:
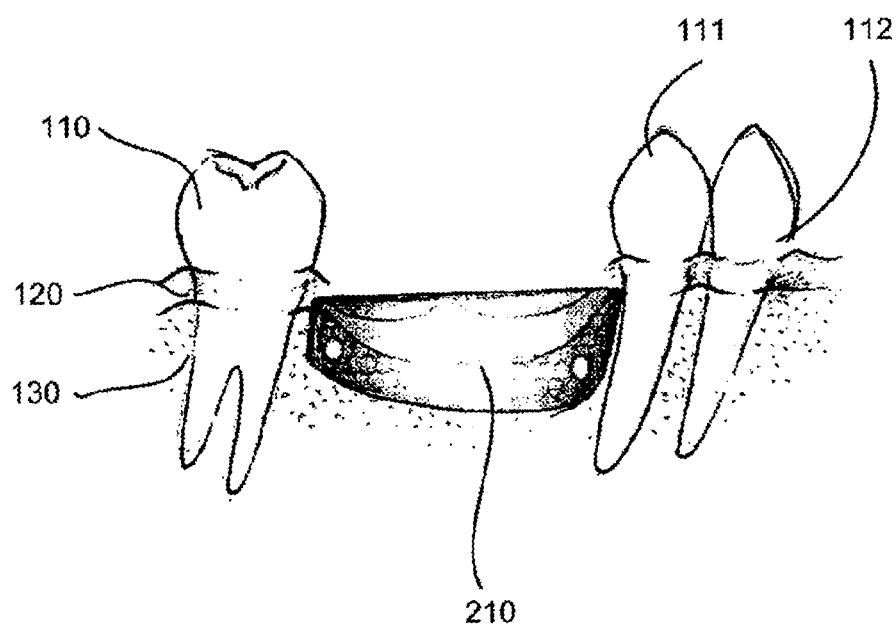
FIGS. 2a to 2i are illustrations of a computer based method of virtually planning a medical procedure, namely of a body portion with insufficient bone structure for a desired aesthetical creation and creation of a sufficient structure by means of a membrane treatment creating an artificial bone structure.

In FIG. 2a a virtual design of a membrane 210 for reconstruction of bone in the interspace 143 shown in FIG. 1c is illustrated. The membrane 210 may be a matrix of a casting form, creating a hollow space in which a bone substitute may be created. The membrane 210 may for instance be a thin piece of metal having a shape configured to a specific anatomical patient situation.

Figure 2B:
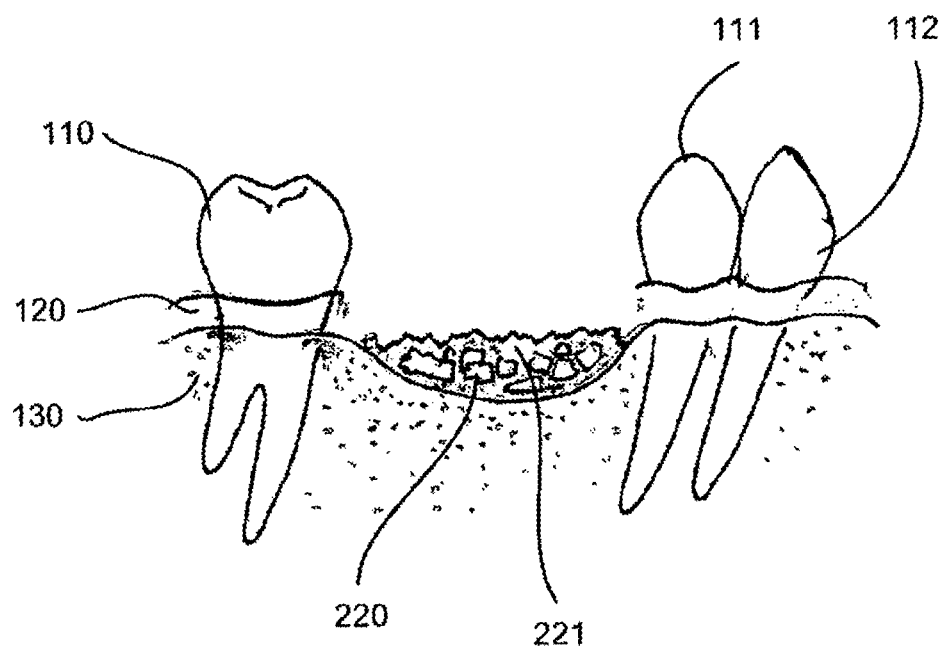

In FIG. 2b a virtual simulation of bone growth is illustrated, for instance by means of bone pieces 220 and BMP 221, or other suitable bone fillers.

Figure 2C:
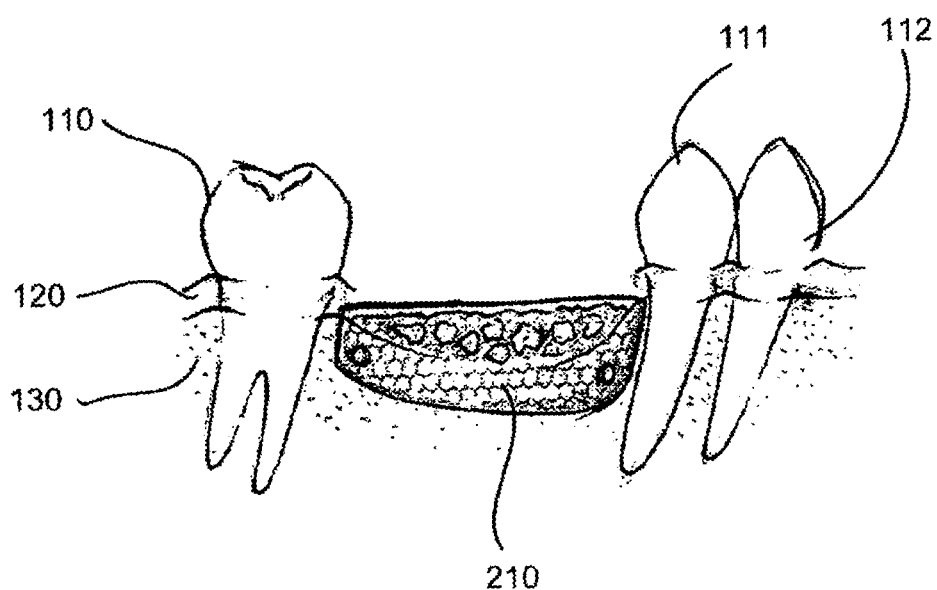

In FIG. 2c a fixation of a membrane 210 is virtually planned, in order to provide a desired created or re-created bone section 230. The grown bone section 230 facilitates an advantageous creation of a dental restoration, e.g. by providing one or more dental implants with a mechanically strong seat in grown bone tissue 230 and previously present bone tissue 130, aesthetically advantageous final results of a dental restorative procedure, etc.

Production data based on the virtual planning may be provided for producing the membrane 210. The virtual planning of a medical procedure comprises providing position data for a position of the occlusion line in relation to the jaw bone tissue 130. Thus a modification of the jaw bone tissue boundary surface at the tooth gap 140 is provided as a function of the position data of the occlusion line.

Figure 2D:
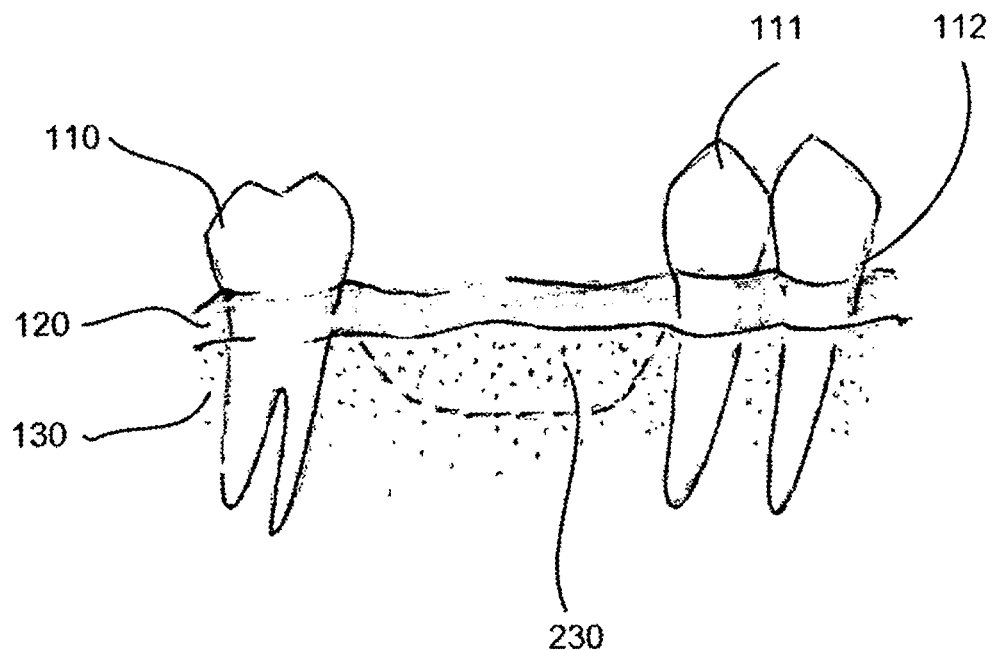
Figure 2E:
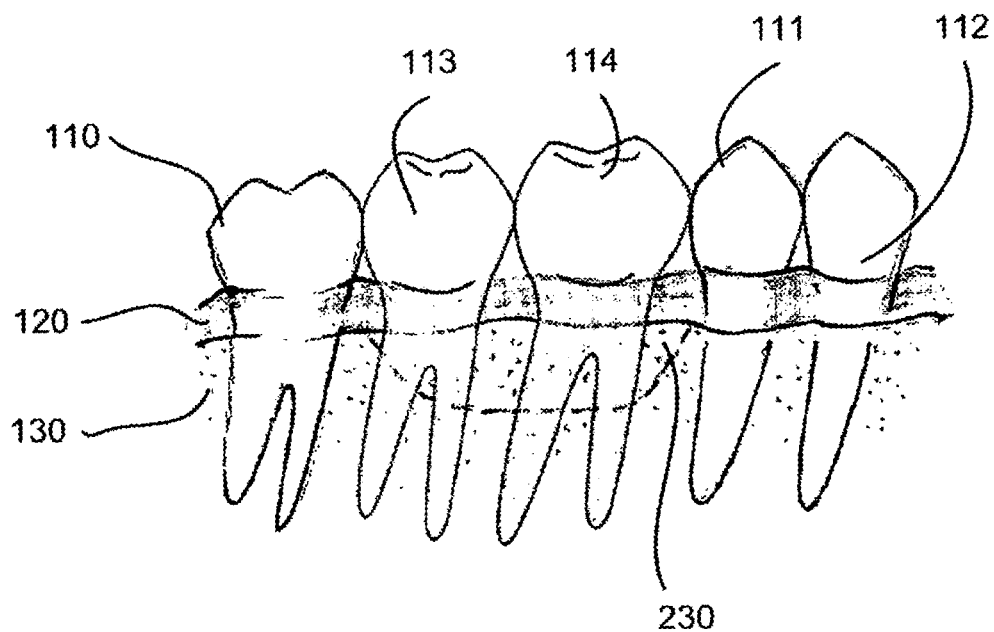

In FIG. 2d a virtual simulation of a recreated bone section 230 is illustrated. Alternatively, or in addition, a real dental restorative procedure may be performed based on the virtual planning illustrated in FIGS. 1a to 1c and 2a to 2c. In this case, the membrane 210 may be produced as a patient configured mass customized medical product and fixed to the patient, as virtually planned. After bone growth of bone tissue 230 is completed, patient data may in this case be registered for the body portion comprising the grown bone tissue 230. The patient data may be used for fine tuning the virtual planning and adapting it to the real patient situation, as illustrated in FIG. 2e where the virtual library teeth 113 and 114 are used for defining a desired final result as explained above.

Figure 2F:
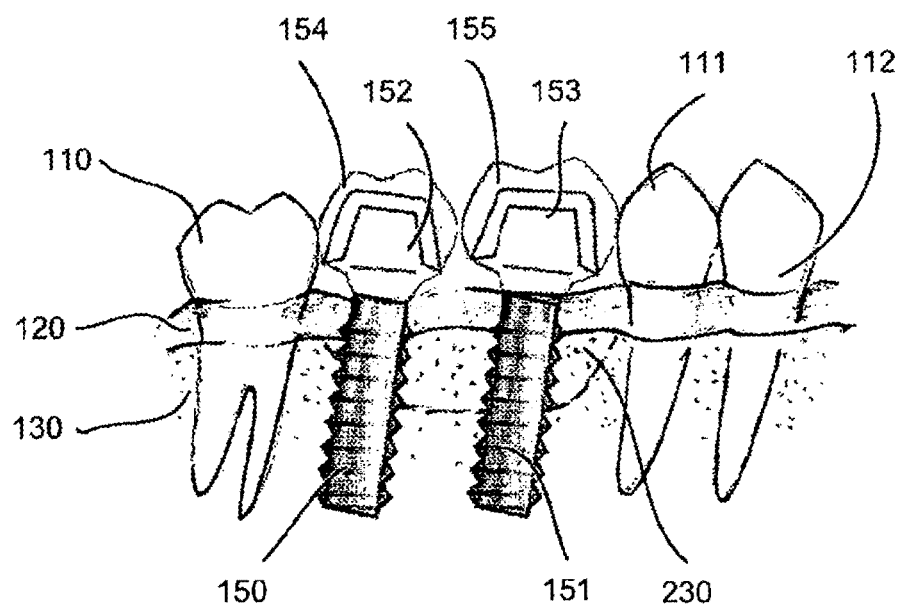

Similar to FIG. 1c, a final result of a virtual planning is illustrated in FIG. 2f. Here, a virtual planned final result of the dental restorative procedure is illustrated with two dental implants 150, 151, comprising threaded portions inserted into the grown bone tissue 230 and the previously existing bone tissue 130. The two dental implants 150, 151 have dental crowns 154, 155 attached at their apical part via suitable abutments 152, 153. The virtual transition from the virtual library teeth 113, 114 to the virtually planned dental implants 150, 151 having dental crowns 154, 154 may be done automatically by means of suitable algorithms, or semi automatically including manual correction of a suggested transition, or completely manually by choosing suitable dental implants from a range of standard sizes and planning of the dental crowns in accordance with the position of the top portion of the library teeth. This virtually planned rehabilitation may be made in a dental planning software, such as Procera® of Nobel Biocare, having a suitable plug in or software routine for virtually planning a bone structure adaptation to a desired final result of a dental restorative procedure.

Figure 2G:
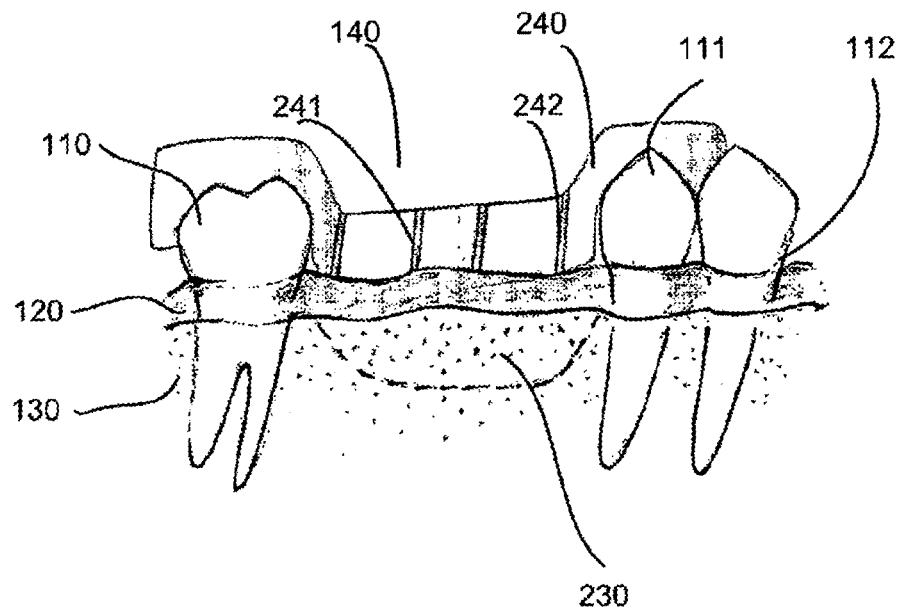

In FIG. 2g, a virtually planned medical product in the form of a surgical template 240 for drill and implant guided surgery with guide sleeves 241, 242 for facilitating drilling of holes for receiving the dental implants 150, 151 is illustrated. Data for producing the surgical template 250 for drill and implant guided surgery, for use in a real dental restorative procedure subsequent to the virtual planning, is provided as an output from the virtual planning. The surgical template 240 for drill and implant guided surgery may be suitably fixed to teeth 110, 111 adjacent to the tooth gap 140. Alternatively, or in addition, the surgical template for drill and implant guided surgery may be fixed to jaw bone tissue by means of anchor pins. The surgical template 240 for drill and implant guided surgery provides at least one drill guide in a desired direction and provides a stop for the drill, thus enabling providing of a hole for receiving a dental implant in a well defined direction and depth in bone tissue 130 and bone implant 160. In the same way, dental implants may be screwed into bone tissue 230, 130, guided by the guide sleeves of the surgical template 240 for drill and implant guided surgery. Production data based on the virtual planning is provided for producing the surgical template 240 for drill and implant guided surgery. A surgical template for positioning implants may also be used in the situations of FIGS. 1e-1f and 4b described below.

Figure 2H:
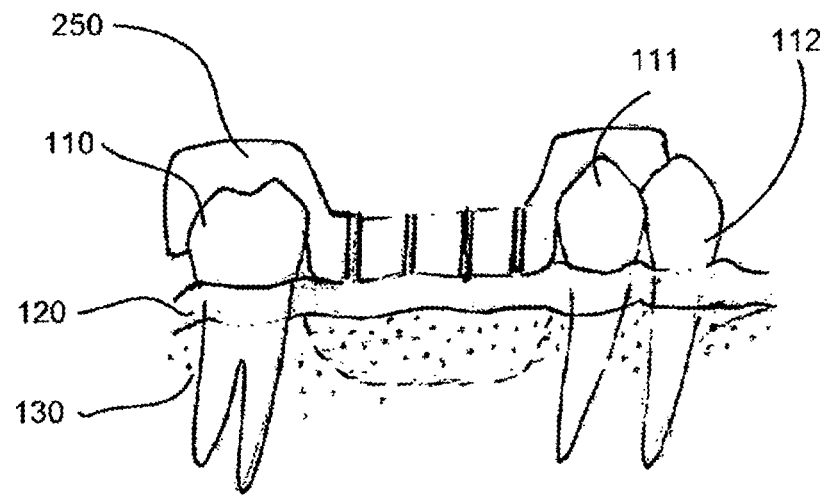

In FIG. 2h the real surgical template 250 for drill and implant guided surgery is illustrated prior to drilling holes and fixating dental implants in the holes.

Figure 2I:
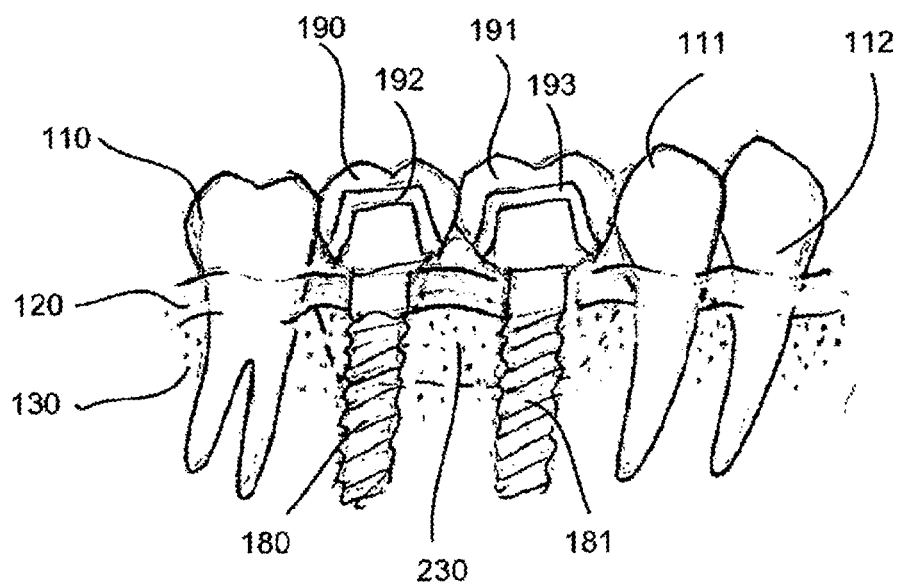

In FIG. 2i the final result of the dental restoration is illustrated, wherein crowns 190, 191 are attached to the dental implants via suitable abutments 195, 196 and by means of a suitable adhesive 192, 193 or other fixation means, such as press fitting or screws.

FIGS. 3a to 3d are illustrations of a computer based method of virtually planning a medical procedure, namely of a body portion with an undesired surplus of a bone structure for a desired aesthetical creation and creation of a suitable bone structure by removal of bone tissue.

Figure 3A:
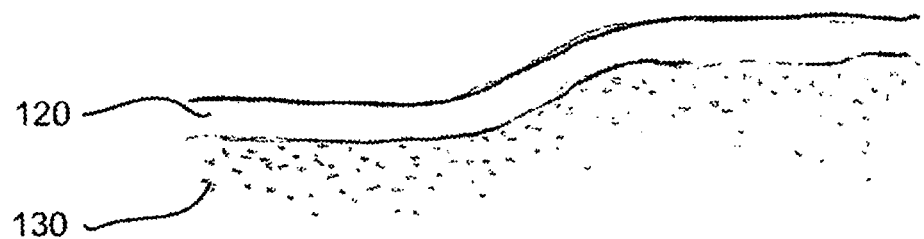
FIGS. 3a to 3g are illustrations of a computer based method of virtually planning a medical procedure, namely of a body portion with an undesired surplus of a bone structure for a desired aesthetical creation and creation of a suitable bone structure by removal of bone tissue.

In FIG. 3a a profile of a crest of a jaw of a patient, including jaw bone tissue 130 and soft tissue 120, is illustrated. The specific topography of the profile may originate from various historical developments thereof, e.g. surgical treatments, loosening or extraction of teeth, etc.

Figure 3B:
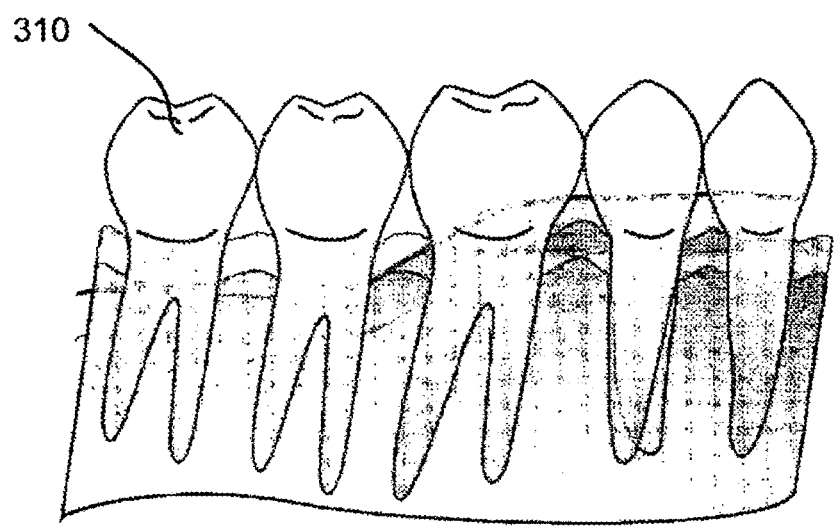

In FIG. 3b a stage of virtual planning a final outcome of a medical procedure, here a dental restorative procedure, is illustrated, including a number of virtual teeth chosen from a tooth library and positioned along the dental arch in the jaw. The positioning of teeth for virtually planning a final outcome of a dental restorative procedure, such as in this present embodiment and other embodiments described herein, may be made according to various methods, e.g. such based on anatomically fixed skull landmarks, such as described in SE0701296-6 of the same applicant as the present application, filed on May 25, 2007 which is incorporated herein by reference in its entirety.

In FIG. 3b it can already be seen that the profile of the bone structure collides with the desired final outcome. The difference in level of the bone topography makes it impossible to provide the desired final outcome, which for instance is based on aesthetical reasons, and/or dental situation requirements, such as a good occlusion, bite index etc.

Figure 3D:
Figure 3C:
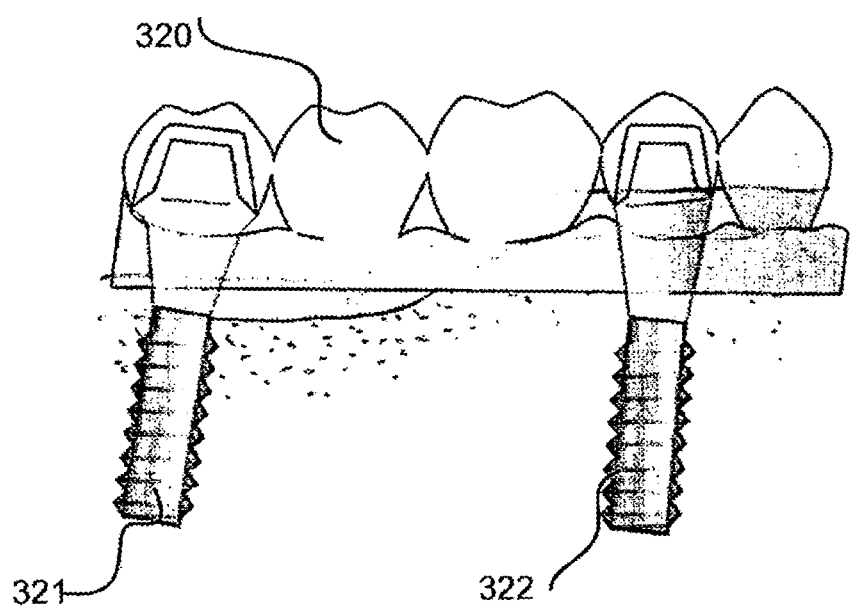

In FIG. 3c the desired final outcome of the virtually planned dental restoration is illustrated, including two dental implants 321, 322 fixed in jaw bone tissue and carrying a bridge 320.

In order to achieve this final outcome, a portion 330 of the bone tissue 130 has to be removed, as is illustrated in FIG. 3d. In this example, the crest of the jaw bone tissue is leveled out as illustrated by the dashed line in FIG. 3d. Based on this virtual planning of bone tissue removal, data for producing a cutting template may be provided. The virtual planning may now be interrupted and the real medical procedure may be performed and new patient data may be input for the situation with removed bone, wherein the final outcome may be fine tuned. Alternatively, the virtual planning of the medical procedure may continue directly and data for producing a surgical template 340 for drill and implant guided surgery is provided.

Production data based on the virtual planning may be provided for producing the surgical template 340 for drill and implant guided surgery. The virtual planning of the medical procedure comprises providing position data for a position of the occlusion line of the bridge 320 in relation to the jaw bone tissue 130. Thus a modification of the jaw bone tissue boundary surface at bone tissue portion 330 is provided as a function of the position data of the occlusion line of the bridge 320.

Figure 3E:
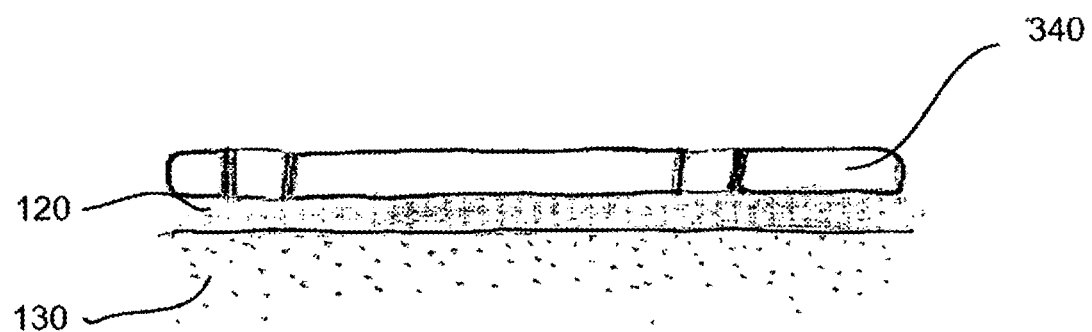
Figure 3F:
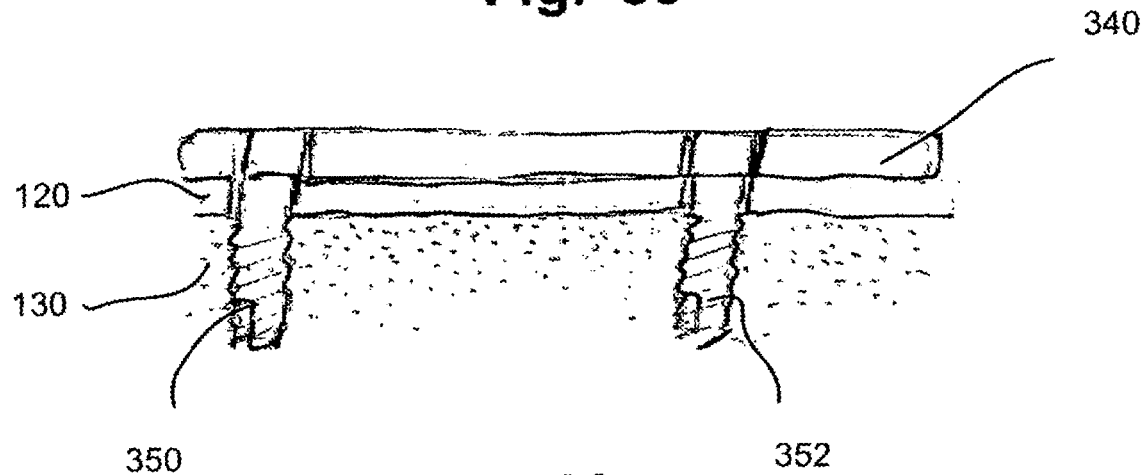
Figure 3G:
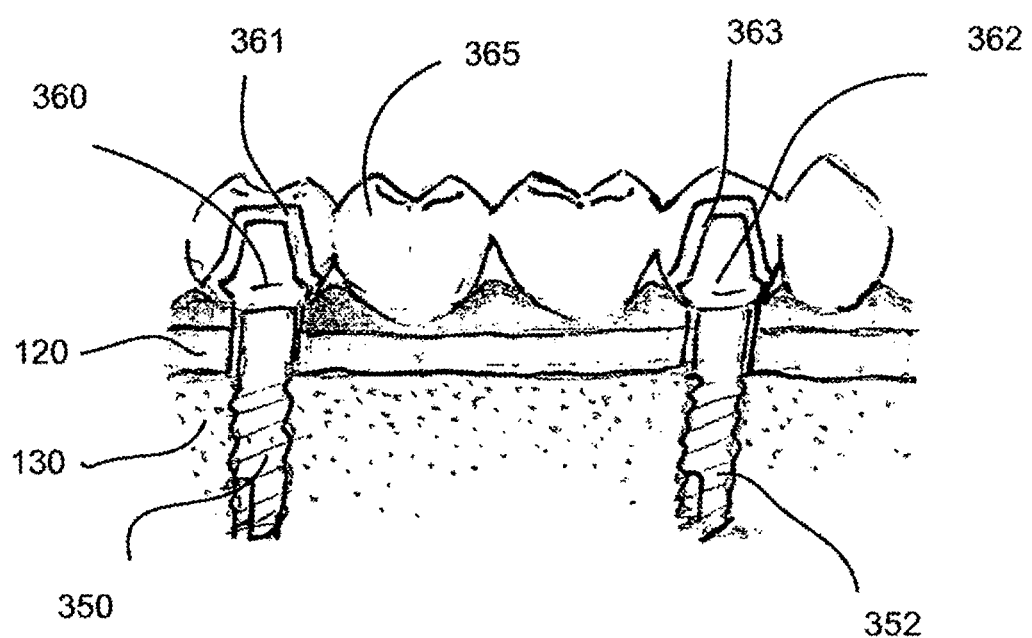

FIGS. 3e to 3g illustrate the real medical procedure that is performed after having adjusted the bone topography to the desired level. The surgical template 340 for drill and implant guided surgery is used for drilling holes in the bone tissue 130, guiding dental implants 350, 352 and fixing the latter in the bone tissue 130. The bridge 365 is fixed to the dental implants 350, 352 using intermediate abutments 360, 362 and distances 361, 362 and/or suitable adhesives. The final outcome of the real medical procedure, as shown in FIG. 3g, corresponds thus to the virtually planned final outcome.

FIGS. 4a to 4i are illustrations of a computer based method of virtually planning a medical procedure and a real medical procedure based on the virtual planning. The medical procedure is a dental restorative procedure of a body portion with insufficient bone structure for a desired aesthetical creation and the procedure comprises creation of a sufficient bone structure by means of a distraction treatment.

Distraction osteogenesis is a surgical process used for the reconstruction of skeletal deformities. The bone is surgically (with a corticotomy) split in two segments. Distraction technology has been used mainly in the field of orthopedics, but the process has shown equally effective in facial skeletal reconstruction.

Virtual planning of a medical procedure may comprise virtual planning of bone distraction. In some embodiments, dental implants are virtually positioned into an existing crest of a jaw bone and relocation of the crest is virtually planned to a preplanned desired final position by means of a virtually planned distraction technique. The virtual planning may provide data for producing a cutting template that is applied to the jaw bone in order to cut loose a portion of the jaw bone that subsequently is continuously moved by means of a distractor unit.

A general description of bone correction methods by means of distraction is for instance described in William Bell DDS, Cesar Guerrero DDS: Distraction Osteogenesis of the Facial Skeleton; ISBN 978-1-55009-344-5; Pub Date: December, 2006.

The desired final position may be virtually planned as described above, for instance by means of a virtual planning using library teeth.

Alternatively, a conventional radiographic guide that is applied in the oral cavity of the patient may be used to provide input patient data to the virtual planning of the dental restorative procedure. The radiographic guide may in this case define the final position of the dental restoration to be provided.

These embodiments are elucidated in more detail below with reference to FIGS. 4a to 4i.

Figure 4A:
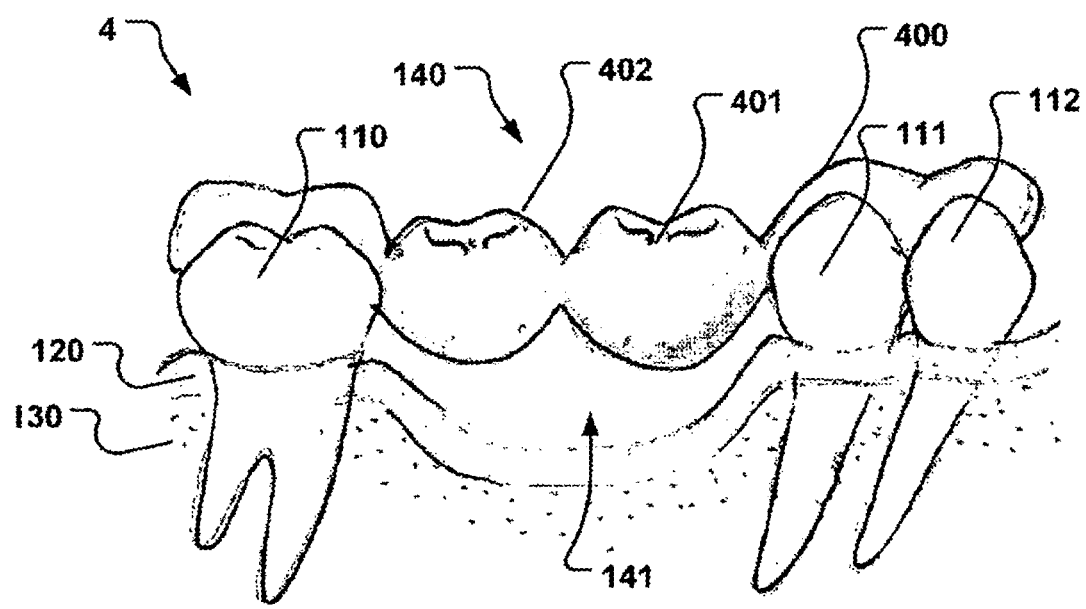
FIGS. 4a to 4i are illustrations of a computer based method of virtually planning a medical procedure, namely of a body portion with insufficient bone structure for a desired aesthetical creation and creation of a sufficient structure by means of a distraction treatment.

FIG. 4a illustrates an anatomical patient situation 4 with insufficient desired aesthetics, similar to FIG. 1a, wherein a virtual radiographic guide 400 is attached to teeth 110, 111, 112 adjacent a tooth gap 140. The virtual radiographic guide 400 comprises the final position of two teeth 401, 402 in the tooth gap 140. The body portion of the patient together with the radiographic guide 400 is digitized using a suitable technique, such as CT, MR, etc. Based on this desired final outcome, a dental restorative procedure is virtually planned. Similar to the embodiments described above with reference to FIGS. 1 and 2, the tooth gap 140 comprises a recess 141 in the jaw crest that has to be adjusted accordingly.

Figure 4B:
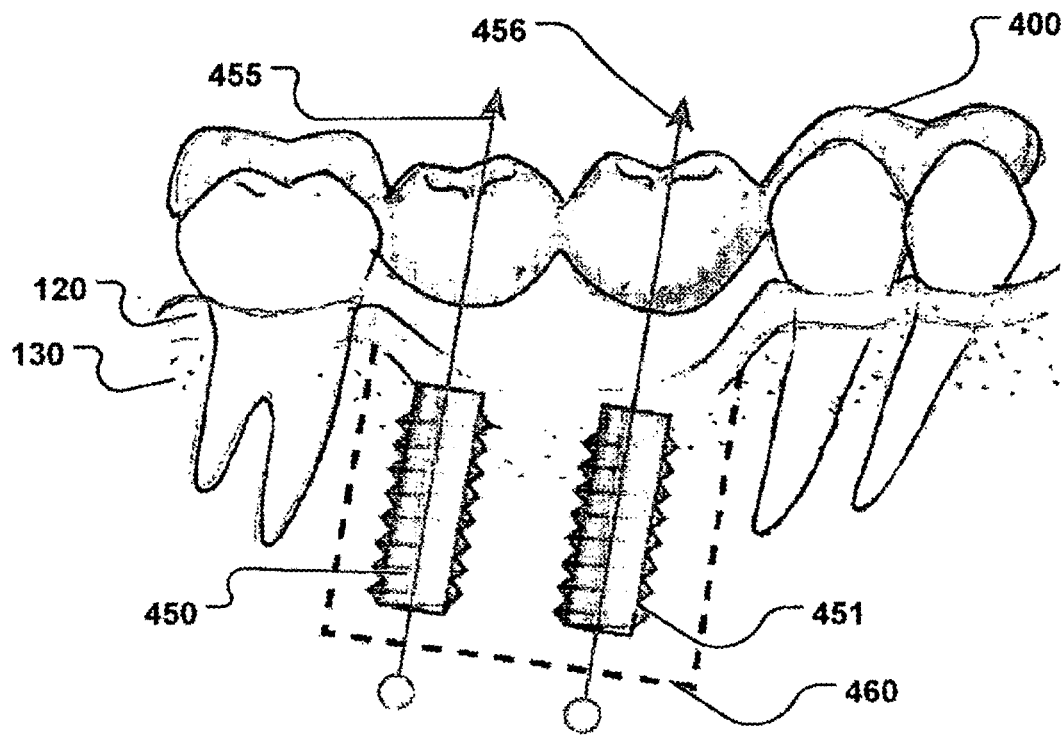
Figure 4C:
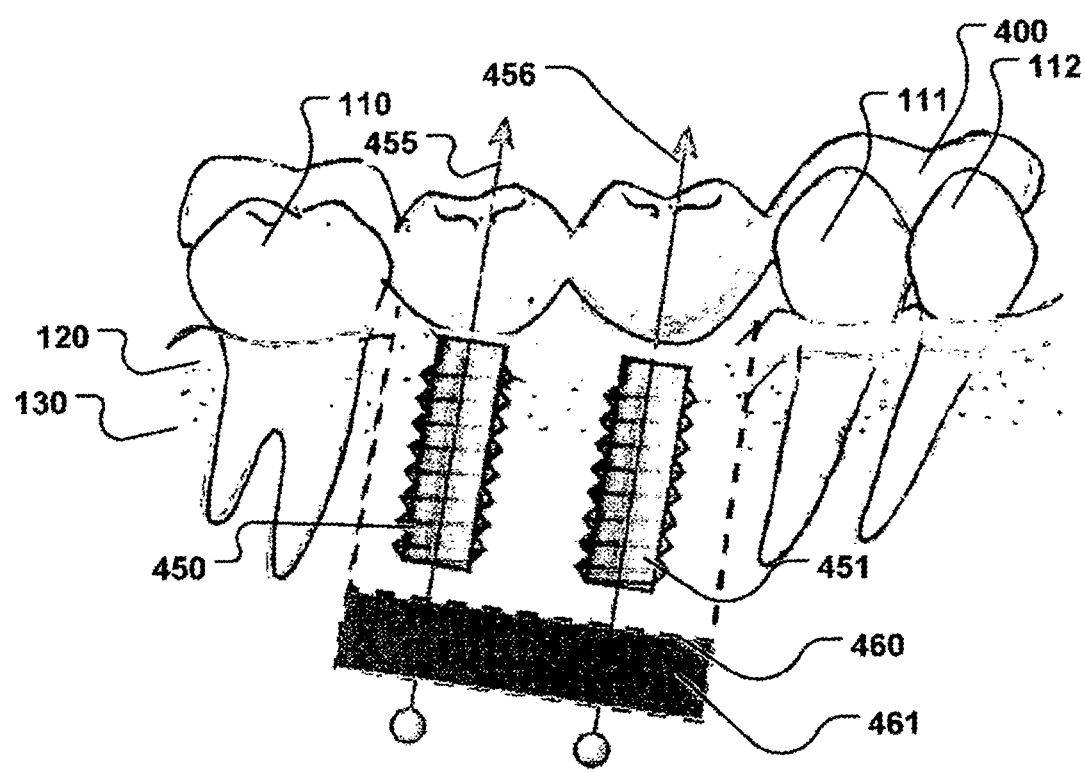

In the present embodiment, the recess 141 in the tooth gap 140 is adjusted by means of a distraction technique, which is virtually planned. As is illustrated in FIG. 4b, a desired position of dental implants 450, 451 in an area of distraction 460 is determined. This may be done by determining a final implant position of the dental implants 450, 451, as shown in FIG. 4c. An area of distraction 460 is determined, as illustrated by the dashed line in FIG. 4b. The arrows 455, 456 in FIG. 4b illustrate the direction of distraction. In this embodiment the direction of distraction of both dental implants 450, 451 is oriented parallel to each other in order to provide a desired distraction of the bone of distraction area 460, as is needed and will be described below. The bone tissue area 461 is created by the distraction process, i.e. continuously, but sufficiently slowly, drawing the distraction area in the direction of arrows 455, 456.

Production data based on the virtual planning may be provided for producing the surgical template 470 for drill and implant guided surgery. The virtual planning of the medical procedure comprises providing position data for a position of the occlusion line of the teeth 401, 402 in relation to the jaw bone tissue 130. Thus a modification of the jaw bone tissue boundary surface at tooth gap 140 is provided as a function of the position data of the occlusion line of the teeth 401, 402.

Based on this virtual planning, data for producing a surgical template for drill and implant guided surgery for inserting the dental implants into the area of distraction may be provided.

Figure 4D:
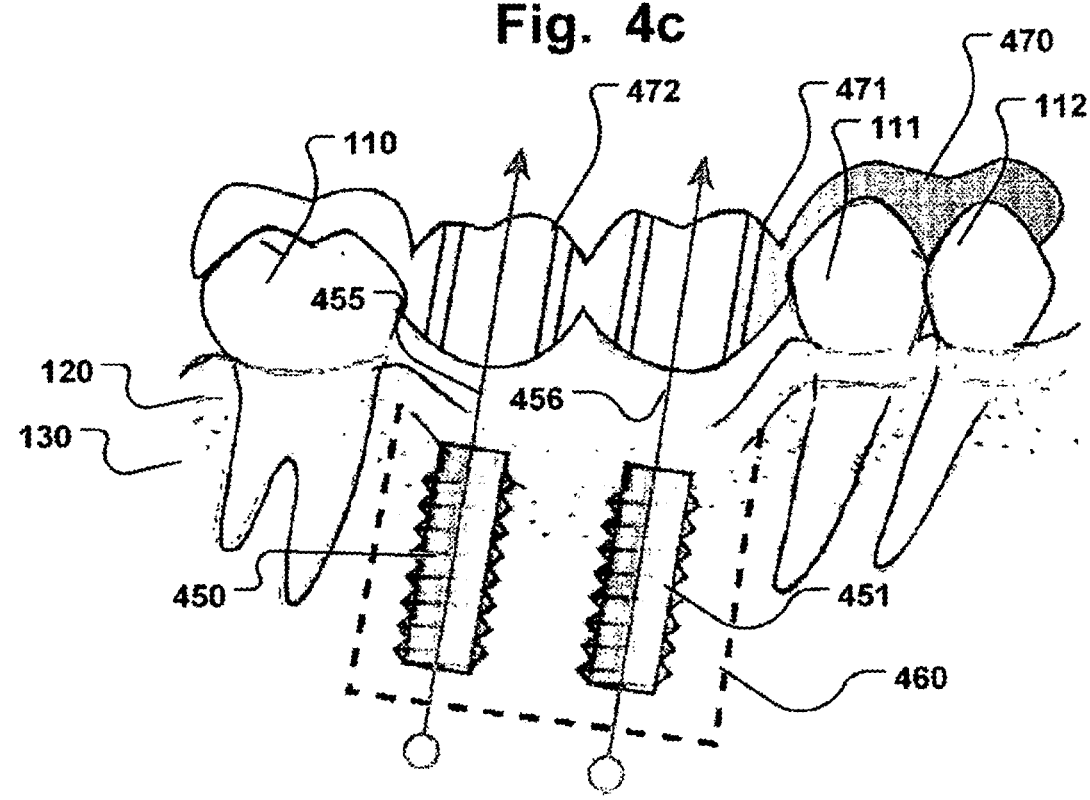
Figure 4E:
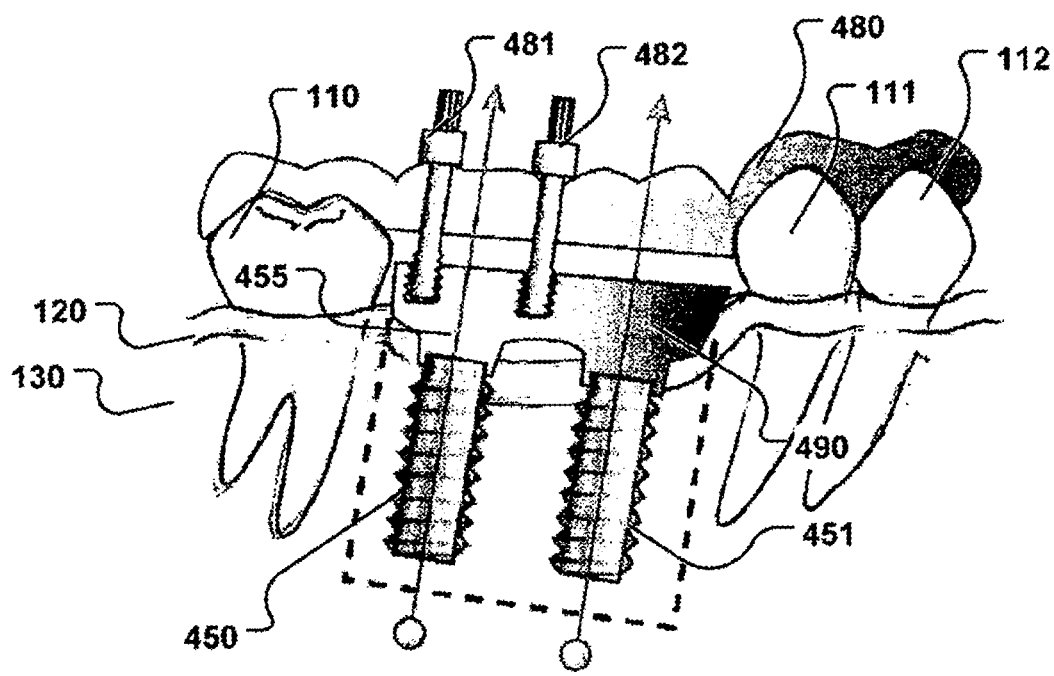
Figure 4F:
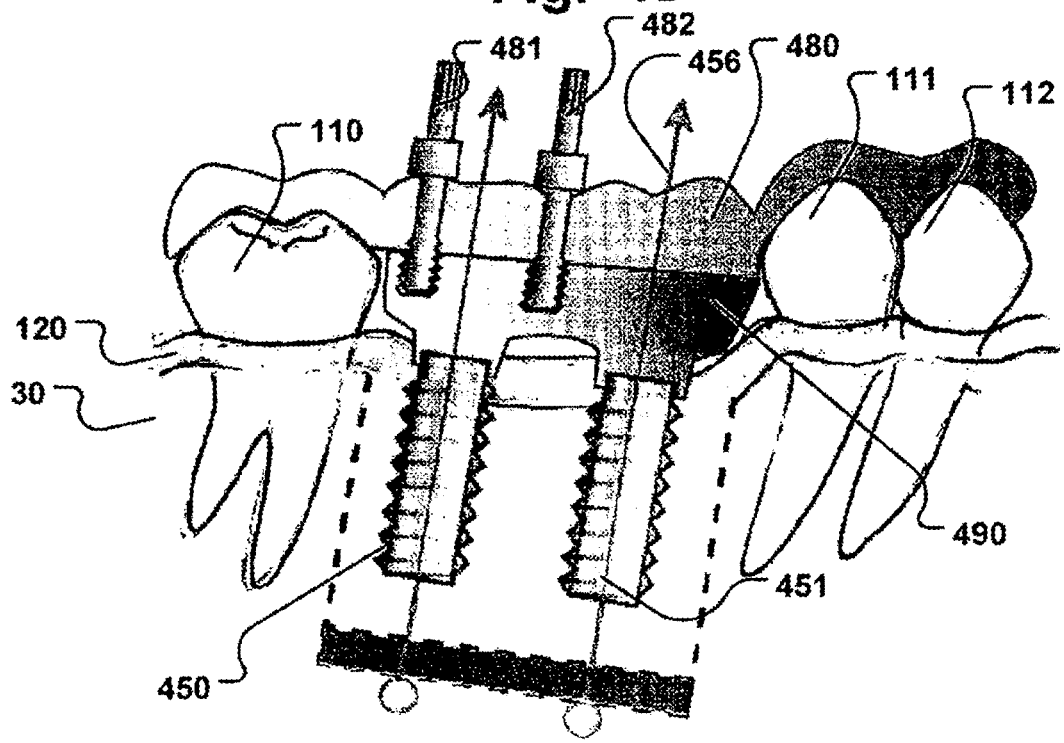

Virtual planning continues with dental implants inserted into the existing bone structure, as shown in FIG. 4b. Data for producing a cutting template may be provided for removing the area of distraction from the surrounding bone tissue. Virtual planning of the surgical template for drill and implant guided surgery and insertion of dental implants 450, 451 is illustrated in FIG. 4d. The surgical template for drill and implant guided surgery comprises guide sleeves 471, 472 for determining a desired orientation and position of the dental implants 450, 451 in the bone tissue 130. Furthermore data for production of a counter holder 480 for providing a counter force for distraction screws 481, 482 directly or indirectly attached to the dental implants 450, 451 may be provided. Data for producing an intermediate distraction module 490 may be generated. The intermediate distraction module may correct a drawing direction between the distraction holder and the dental implants, as shown in FIGS. 4e and 4f. Virtual planning continues with simulation of the bone tissue in the area of distraction being drawn up to the desired level, wherein bone 461 growing into the artificially created gap of the distraction fills the gap continuously, resulting in the situation shown in FIG. 4c.

Figure 4G:
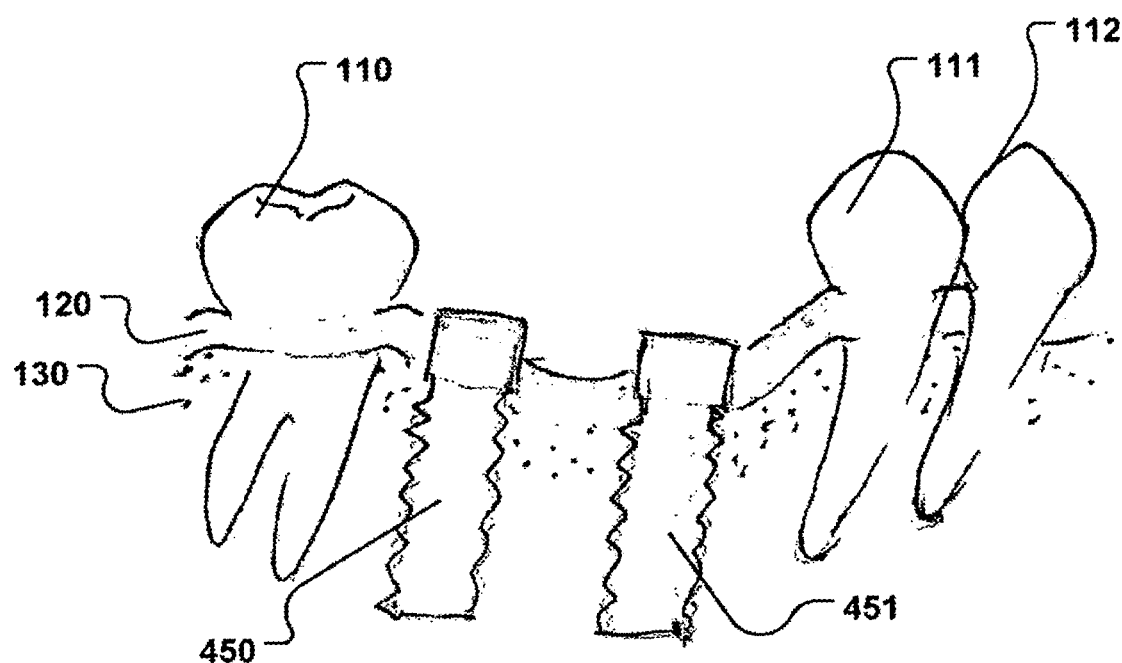
Figure 4H:
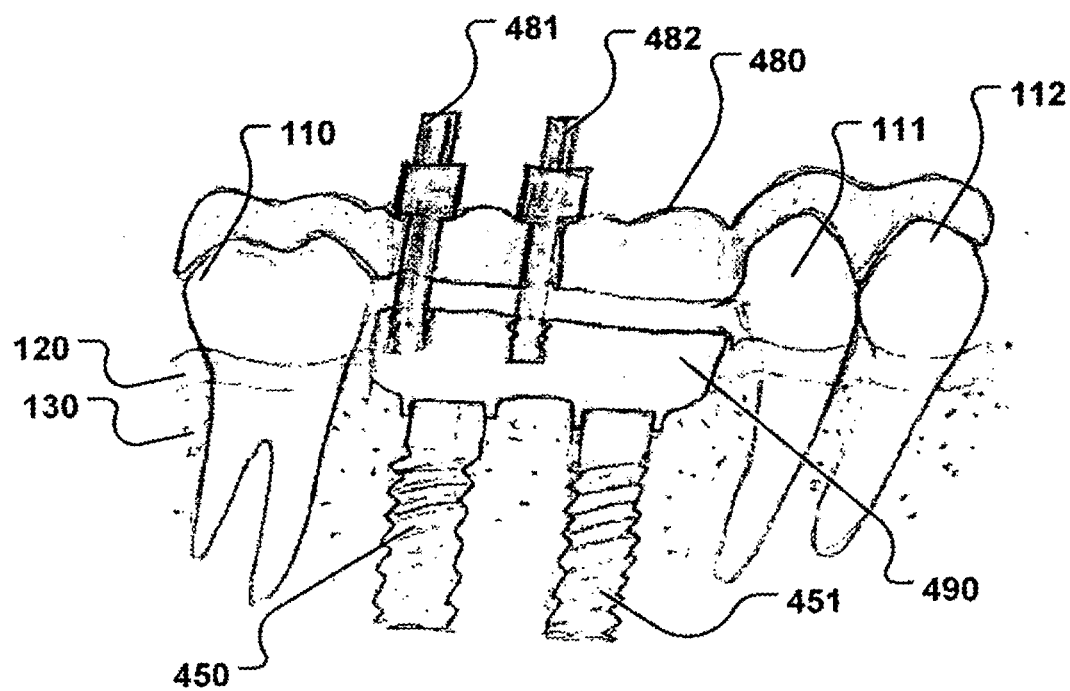
Figure 4I:
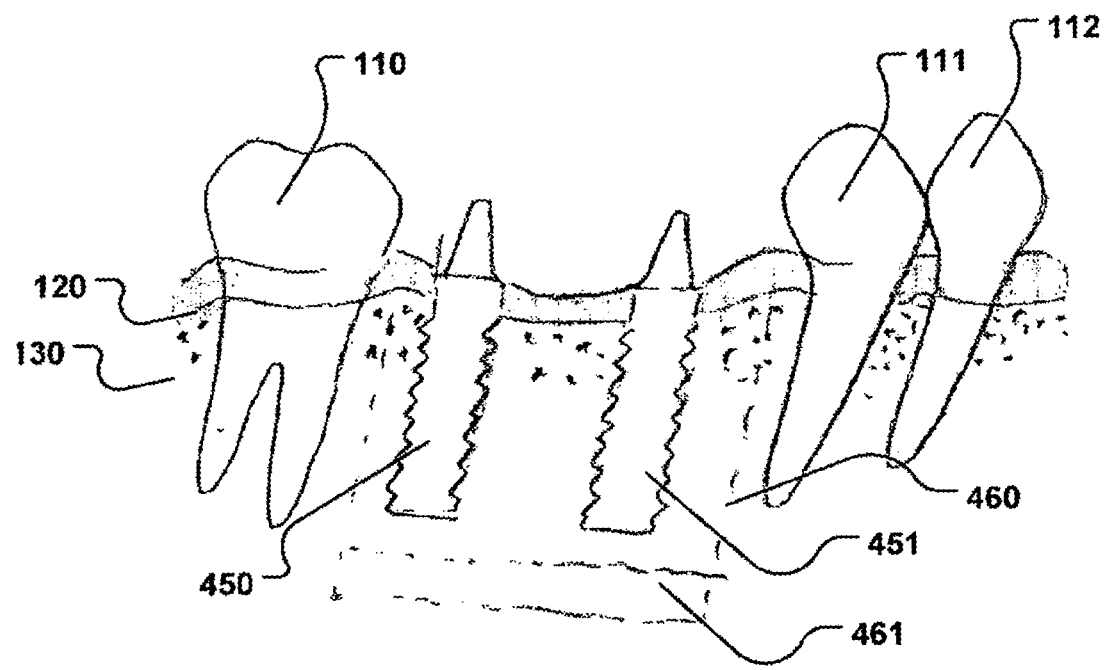

Subsequently, the real dental restorative procedure is performed, as illustrated in FIGS. 4g to 4i.

In FIG. 4g two dental implants 450, 451 are shown positioned in the jaw bone tissue 130 by using a surgical template for drill and implant guided surgery (not shown), produced from data of the previous virtual planning. The implants are thus fixed in the bone tissue 130.

In FIG. 4h a counter holder 480 for providing a counter force for distraction screws 481, 482 is directly or indirectly attached to the dental implants 450, 451, as is illustrated. The counter holder 480 is produced from data of the previous virtual planning. An intermediate distraction module 490 between the distraction holder and the dental implants is used, as shown in FIG. 4h. The intermediate distraction module 490 may be used to achieve the parallel distraction movement of the distraction area 460 in case the distraction screws 481, 482 cannot be arranged in parallel or directly to the dental implants. The counter holder 480 may be attached to adjacent teeth 110, 111, 112 or alternatively or in addition to other elements having a fixed position in relation to the desired final position of the distraction area 460, e.g. by means of anchor pins in jaw bone tissue 130 and/or implants outside the distraction area. In FIG. 4i the finished distraction is illustrated. Subsequently, the dental restoration is finished by attaching suitable, previously virtually planned, dental restorations, such as a bridge or crowns, to the dental implants. In this manner the previously virtually planned final outcome is provided.

Bone Substitute

Biodegradable bone substitute are known in the art and may be used in the medical procedures that are virtually planned according to some embodiments. Bone substitute or replacement material, e.g. polymeric material, may be used to avoid bone transplantation procedures that are less patient convenient.

For instance, in U.S. Pat. No. 5,278,202, which is incorporated herein by reference in its entirety, biodegradable in-situ forming implants and methods of producing the same are disclosed. A biodegradable polymer is provided for use in providing syringeable, in-situ forming, solid biodegradable implants for animals. The polymer is placed into the animal in liquid form and cures to form the implant in-situ. A thermoplastic system to form the implant comprises the steps of dissolving a non-reactive polymer in biocompatible solvent to form a liquid, placing the liquid within the animal, and allowing the solvent to dissipate to produce the implant. An alternative, thermosetting system comprises mixing together effective amounts of a liquid acrylic ester terminated, biodegradable prepolymer and a curing agent, placing the liquid mixture within an animal and allowing the prepolymer to cure to form the implant. Both systems provide a syringeable, solid biodegradable delivery system by the addition of an effective level of biologically active agent to the liquid before injection into the body.

In U.S. Pat. No. 5,077,049, which is incorporated herein by reference in its entirety, a biodegradable system for regenerating the periodontium is disclosed. Methods are described for assisting the restoration of periodontal tissue in a periodontal pocket and for retarding migration of epithelial cells along the root surface of a tooth. The methods involve placement of an in-situ forming biodegradable barrier adjacent the surface of a tooth. The barrier is microporous and includes pores of defined size. The barrier can include a biologically active agent.

In U.S. Pat. No. 6,206,920, which is incorporated herein by reference in its entirety, a composition and method for forming biodegradable implants in situ and uses of these implants are disclosed. The invention discloses a composition having a mixture of a pharmaceutically, medically or veterinarily acceptable polymer, preferable a poly (lactic-co-glycolic acid) copolymer (PLGA) containing between about 10 and 100 wt. % lactic acid (LA) units, preferably between about 50 and 90 wt. % LA units, and alpha-(tetrahydrofuranyl)-omega-hydroxypoly(oxy-1,2-ethandiyl) (glycofurol). Methods of forming solid implants in situ in an animal body, the implants optionally comprising a drug or other biologically active agent, as well as the use of the compositions of the invention in the treatment of animal bodies, are also disclosed.

In U.S. Pat. No. 5,885,829, which is incorporated herein by reference in its entirety, engineering of oral tissues is disclosed. Disclosed are methods for regenerating dental and oral tissues from viable cells using ex vivo culture on a structural matrix. The regenerated oral tissues and tissue-matrix preparations thus provided have both clinical applications in dentistry and oral medicine and are also useful in in vitro toxicity and biocompatibility testing.

In U.S. Pat. No. 6,409,764, which is incorporated herein by reference in its entirety, methods and articles for regenerating bone or peridontal tissue are disclosed. There are numerous medical situations involving deficiencies of living bone or periodontal tissue and where increase of living bone or periodontal tissue mass is desired. Methods are described wherein a configured, shell-like device that is capable of being penetrated by living cells and tissues, is implanted into the body of a mammal in such a way as to establish a space, the space being at least partly, bounded by the device. The configuration of the device is such that the configuration of the established space is essentially the same as the configuration of living bone or periodontal tissue that is desired for treatment of the tissue deficiency. At least one protein from the Transforming Growth Factor-Beta Superfamily of proteins is placed within the established space for the purpose of stimulating the growth of living bone or periodontal tissue within the established space. A kit for the generation of living bone or periodontal tissue, comprised of the components mentioned above, is also disclosed.

In U.S. Pat. No. 4,787,906, which is incorporated herein by reference in its entirety, a controlled tissue growth and graft containment are disclosed. A device and technique for restoring the alveolar ridge of the human jawbone in the edentulous state. Such device involves an inert, porous tube which contains granules whereby when the device is in place on the ridge, tissue growth occurs from living bone through the porous tube inwardly or outwardly from the granular filler. The tube prevents the granules from migrating.

In U.S. Pat. No. 4,542,539, which is incorporated herein by reference in its entirety, a surgical implant having a graded porous coating is disclosed. This biologically compatible surgical prosthetic implant has a multi-layer coating formed from metallic particles having sizes which increase in the direction from the metallic body of the implant toward the surface of the coating which is to interface with bone. The gradation is achieved by first depositing a layer of small particles, for example microspheres, of metallic coating material on the surface of the implant, then depositing progressively larger particles in subsequent layers. The particles may be deposited by any one of a number of well-known processes including but not limited to a flame-plasma process, in which several parameters are controlled as functions of the size of the particles. The resultant coating has minimum density and maximum porosity at its outer surface to encourage ingrowth of bone. The density of the coating is maximized at the interface between the coating and the body of the implant, thereby substantially matching the mechanical and thermal properties of the body of the implant and the coating and achieving optimum adherence of the coating to the body of the implant.

In U.S. Pat. No. 5,839,899, which is incorporated herein by reference in its entirety, a method and apparatus for growing jaw bone utilizing a guided-tissue regeneration plate support and fixation system are disclosed. A method of growing jaw bone and the related guided-tissue regeneration plate support and fixation system employed in the method where an isolated and protected space free from tissue impingement, occlusal loading, chewing forces or muscular pressure is created between the periosteum and the jaw bone. This space is created by first placing either a dental implant or a guided-tissue regeneration plate support and fixation system tenting-type support screw into the jaw bone. The plate portion of the guided-tissue regeneration plate support and fixation system, preferably made out of Grade 1 commercially pure titanium, being thicker and more rigid in the center, more supportive area and thinner at the periphery is either snapped-down onto the head of the support screw or onto a specialized and modified healing screw of a dental implant which has a receiver cap or is screwed directly into a dental implant. The plate is then bent and molded into the proper shape. In essence, the pliable, moldable plate is both supported by the dental implant or support screw and fixed into place by the same screw creating both support and fixation of the plate giving a precise space below its surface to grow bone. This plate portion can be solid or perforated, and it can be porous or non-porous.

In U.S. Pat. No. 5,297,563, which is incorporated herein by reference in its entirety, a guided bone and tissue generation device and method to be used during or after dental surgery or jaw surgery are disclosed. The disclosure relates generally to methods and devices for facilitation of tissue and bone guided regeneration of a bony deficit. A mechanical barrier dimension to cover the deficit is provided as are means for securing the barrier in place.

In U.S. Pat. No. 7,122,205, which is incorporated herein by reference in its entirety, bioerodable polymeric adhesives for tissue repair are disclosed. Methods for tissue repair are provided employing a matrix comprising a biocompatible, bioerodable polymer, the polymer comprising a thermoplastic lactide-containing terpolymer of monomer units derived from lactic acid, glycolic acid, and either caprolactone or valerolactone, which has a water solubility of about 0.01 to about 500 mg/mL at about 25° C. and adhesive strength of about 600 to about 150,000 Pa and applying the matrix to a tissue defect. The matrix or adhesive can further comprise a filler or a bioactive agent, or both.

The above mentioned disclosures may be used in embodiments for providing virtual planning of medical procedures taking into consideration the described materials, devices and methods.

Bone Transplantation

Alternatively, bone harvesting may be virtually planned to provide suitable bone geometries. Data for a cutting template may be provided from the virtual planning. The cutting template may be used to harvest at least one piece of bone from a suitable body portion of the patient. The cutting template facilitates harvesting the piece of bone that in this manner is provided with a shape suitable for fitting into the body region where the virtually planned medical procedure is performed, e.g. to fill a bone gap in a jaw, in order to modify a bone tissue boundary surface. The piece of bone may thus conveniently be used to replace or create a bone structure in another body portion of the patient. This has also the advantage that immune reactions of the body are mostly avoided as no foreign material is used for creation of bone structures in the patient.

Free Form Fabrication

Free Form Fabrication, FFF is the name of the technology and equipment required to fabricate parts directly from 3-D CAD information. A free form of a solid may be reproduced entirely. In producing an object, e.g. of metal, may comprise completely open ducts, holes and obtuse angles and planes may be reproduced in one swoop.

Free Form Fabrication

In WO04054743A1 of Arcam an arrangement for production of a three-dimensional product comprising a work bench and an irradiation gun within a casing, and a powder dispenser partially outside the casing are disclosed. WO04054743A1 is incorporated herein by reference in its entirety.

Arcam is a high-tech company which has developed an FFF technology (Free Form Fabrication) which makes possible the direct production of solid objects from metal powder, based on 3D CAD models. The technology shortens considerably the production time of injection molding and die-casting tools, thereby meeting a growing need within the manufacturing industry to reduce the lead-time from design to finished product.

For instance, the Arcam EBM S12 is developed for Free Form Fabrication (FFF®) of components in solid titanium and steel directly from CAD, and offers unique geometrical possibilities for manufacturing in titanium and steel.

During an Electron Beam Melting (EBM) process, an electron beam melts metal powder in a layer-by-layer process to build the physical part. Mass customized implants may thus be manufactured quickly and cost-efficiently. For instance bone prosthesis as describe above may thus conveniently be made based on output data from the virtual planning.

Alternative Solid Free Form Fabrication techniques comprise fused deposition modeling and three-dimensional printing techniques.

These and other techniques of Solid Free Form Fabrication may use other materials than metal, e.g. ceramics, glass-ceramic as well as ceramic-matrix and polymer-matrix composite materials. Alumina, zirconia, mullite, silica, spinel, tricalcium phosphate, apatite, fluoroapatite, hydroxyapatite and mixtures thereof are representative ceramic materials which can be used in such solid free form fabrication techniques. Composite materials for use in the invention include a polymeric matrix with particulate or fiber filled components. The polymeric matrix element of the fiber-reinforced and particulate-filled composites may be selected from those known in the art of dental materials, including but not being limited to polyamides, polyesters, polyolefins, polyimides, polyarylates, polyurethanes, vinyl esters or epoxy-based materials. Other polymeric matrices include styrenes, styrene acrylonitriles, ABS polymers, polysulfones, polyacetals, polycarbonates, polyphenylene sulfides, and the like. Such materials, may also be used within the context of the present application, e.g. for providing bone tissue substitute elements, or medical products related to providing a bone structure in body portion of a patient.

In US20040254668A1, which is incorporated herein in its entirety, a macro-porous hydroxyapatite scaffold compositions and freeform fabrication method thereof are disclosed. A solid freeform fabrication method and composition for preparing a calcium phosphate-based macro-porous scaffold for tissue engineering applications. The method includes (A) preparing a mixture of dry solid powder particles in a powder container; (B) preparing a fluid component in a reservoir separate from the powder container; wherein the powder mixture and the fluid component, separately or in combination, comprise at least a calcium source and a phosphoric acid source; (C) operating a material deposition system comprising a liquid deposition device for dispensing the fluid component from the reservoir and a solid powder-dispensing device for dispensing the solid powder mixture from the powder container to selected locations on a target surface of an object-supporting platform, wherein the dispensed fluid and dispensed powder components react to form a calcium phosphate composition (particularly hydroxyapatite or its derivative); and (D) during the operating step (C), moving the deposition system and the object-supporting platform relative to one another in X-Y-Z directions to form the scaffold containing macro pores, greater than 50 mum in size.

Mass customized individual medical products may for instance comprise a dental bridge, abutment, coping, bridge framework, cutting template, surgical template, surgical template for drill and implant guided surgery, bone implant, patient specific membrane, etc.

Planning parameters may for instance comprise:
For an implant, such as dental implant, direction, depth, distance to other structures, estimated mechanical strength, etc.
For a guide sleeve of a surgical template for drill and implant guided surgery for instance direction, depth, position, etc.
For a membrane for instance size, shape, position, material.
For planning of dental implants for instance the position and direction of an exit hole is preferably planned centrally or in the middle of a prosthesis, for instance in order to provide an advantageous mechanical strength of the assembly of implant and prosthesis, and avoiding undue strain on the prosthesis, implant, or surrounding bone tissue, and for aesthetic reasons.
Position of teeth in anatomically correct positions, e.g. with reference to anatomically fixed reference points.
Form, contour, length, thickness, depth, etc. of various components, such as bridges, dental implants and abutments.
Cutting templates: desired shape, contour, direction, etc.
Planning may be based on surface matching, e.g. for providing an advantageous occlusion.
Planning may be modified via a human interface unit, e.g. by clicking on various components and mouse manipulations thereof.

Figure 6:
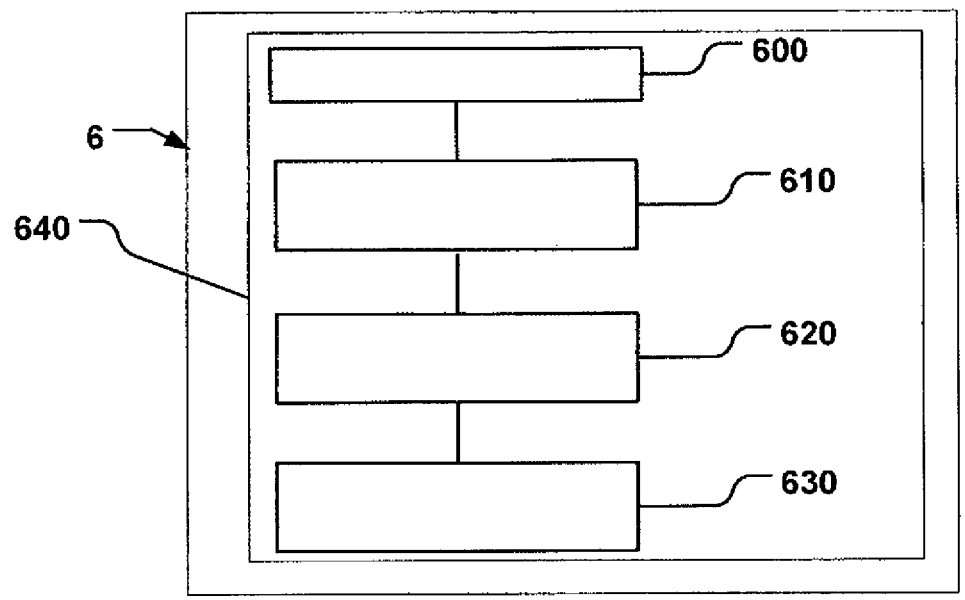
FIG. 6 is a schematical illustration of a system for virtually planning a medical procedure.

FIG. 6 is a schematical illustration of an embodiment of a system for virtually planning a medical procedure.

The system 6 provides computer-based planning of a medical procedure, such as a dental restorative procedure of a patient. The system 6 comprises a unit 600 for virtual planning of a medical procedure of a patient. The system 6 is devised for providing a computer-implemented virtual planning of the medical procedure, wherein the medical procedure comprises providing a patient configured bone structure in a body portion of the patient, such as for instance described in the above embodiments of the method. The system comprises a unit 610 for generating production data based on the virtual planning, wherein the production data is configured for subsequent use in production of the bone structure or a medical product. The medical product is devised for use in the medical procedure, and devised for arrangement in the patient for facilitating the medical procedure, such as a bone implant, membrane, distraction holder, surgical template for guided surgery. The system 6 for virtual planning of a medical procedure comprises a unit 620 for providing position data for a position of at least a part of a prosthesis component in relation to the body portion, such as the occlusion line, of a final outcome of the medical procedure. Furthermore, the system comprises a unit 630 for virtual planning of a modification of a boundary surface at the body portion as a function of the position data, e.g. modifying a jaw bone crest as for instance in the above described examples and embodiments of the method. Units 600, 610, 620, 630 may be implemented in a medical workstation 640 and provided by software code portions run by the workstation 640.

The medical workstation 640 comprises the usual computer components like a central processing unit (CPU), memory, interfaces, etc. Moreover, it is equipped with appropriate software for processing data received from data input sources, such as data obtained from CT scanning, 3D scanning, digital images, etc.

Figure 7:
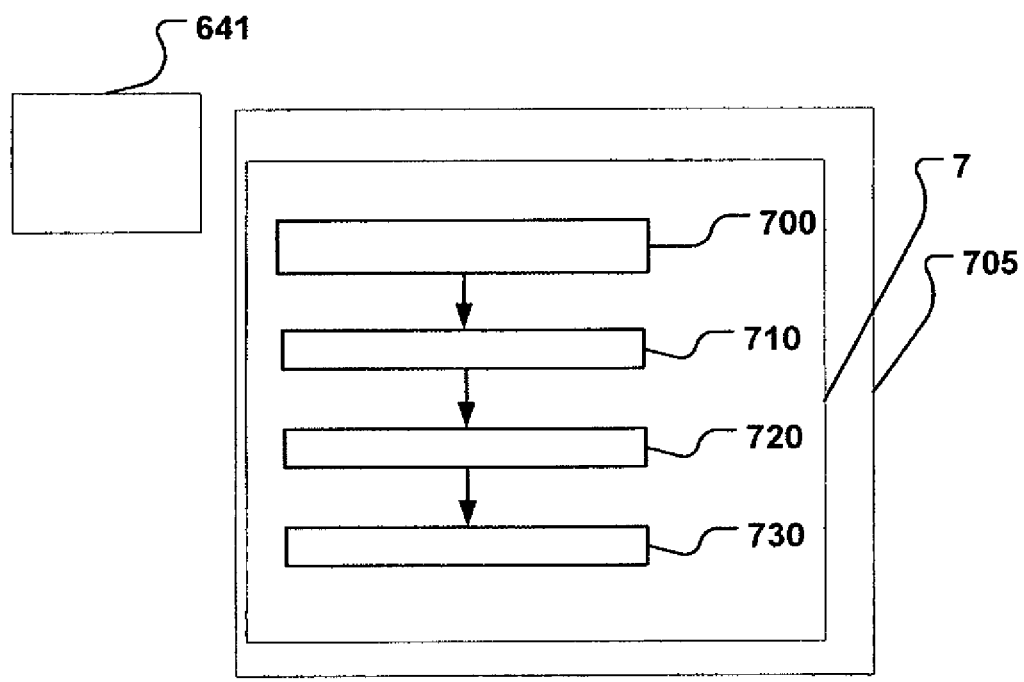
FIG. 7 is a schematical illustration of a computer program stored on a computer readable medium for virtually planning a medical procedure.

FIG. 7 is a schematical illustration of a computer program 7 stored on a computer readable medium 705 for virtually planning a medical procedure. The computer program 7 is provided for processing by a computer 641. The computer 641 may be implemented as the medical workstation 640 or be a processing unit thereof, such that the computer program may be run on the medical workstation 640. The computer readable medium 705 may comprise the computer program 1940 in form of software comprising suitable code segments 700, 710, 720, 730 for performing the virtually planning. The computer program 7 comprises a first code segment 700 for virtual planning of a medical procedure of a patient, e.g. interactively with a user, semi automatically or fully automatically. The medical procedure comprises providing a patient configured bone structure in a body portion of the patient. The computer program 7 comprises a second code segment 710 for generating production data based on the virtual planning, wherein the production data is configured for subsequent use in production of the bone structure or a medical product and wherein the medical product is devised for use in the medical procedure, and devised for arrangement in the patient for facilitating the medical procedure. The computer program 7 comprises a third code segment 720 for providing position data for a position of at least a part of a prosthesis component in relation to the body portion. Moreover, the computer program 7 comprises a fourth code segment 730 for virtual planning of a modification of a boundary surface at the body portion as a function of the position data.

The computer program 7 may for instance be stored on a computer readable medium 705, accessible by the medical workstation 640.

The medical workstation 640 further comprises a monitor, for instance for the display of rendered visualizations, as well as suitable human interface devices, like a keyboard, mouse, etc., e.g. for manually fine tuning the automatical planning otherwise provided by the software. The medical workstation may be part of the system 6. The medical workstation may also provide production data.

For the virtual planning, patient data, e.g. from a CT scan, is imported into a software for pre-surgical planning of the medical procedure, such as a dental restorative procedure, for instance run on the medical workstation 640. The medical workstation 640 may have a graphical user interface for computer-based planning of the medical procedure. The graphical user interface may comprise components for visualizing the methods described above in this specification or recited in the attached claims.

A result of a virtual planning of the medical procedure may be provided to a user in a graphical user interface on the medical workstation 640. Adaptation of bone structures or surface boundaries thereof may be made by means of the human interface devices of the medical workstation 640 interacting via the graphical user interface provided on the monitor thereof.

The present invention has been described above with reference to specific embodiments. However, other embodiments than the above described are equally possible within the scope of the invention. Different method steps than those described above, performing the method by hardware or software, may be provided within the scope of the invention. The different features and steps of the invention may be combined in other combinations than those described. The scope of the invention is only limited by the appended patent claims.

What is claimed is:

1. A computer-implemented method comprising
    virtual planning of a medical procedure of a patient, which medical procedure comprises providing a patient configured bone structure in a jaw bone of said patient, said medical procedure comprising the removal or the distraction of an existing jaw bone structure; and
    generating production data based on said virtual planning, wherein said production data is configured for subsequent use in production of a cutting template, which is devised for use in said medical procedure, and devised for arrangement in said patient for facilitating said medical procedure by providing guidance when cutting a jaw bone structure,
    wherein said virtual planning of the medical procedure comprises using a graphical user interface to input into a software run on a medical workstation position data for a position of at least a part of a dental restoration in relation to said jaw bone and displaying on a monitor of the medical workstation a rendered visualization of the position of the at least a part of said dental restoration in relation to said jaw bone, and
    virtual planning of a modification of a boundary surface at said jaw bone as a function of said position data, wherein said virtual planning comprises the planning of cutting a jaw bone structure, said planning generating the production data for use in the production of said cutting template.

2. The method according to claim 1, wherein said position data comprises position data of a contour of said dental restoration as a virtually planned final outcome of said medical procedure.

3. The method according to claim 2, wherein said dental restoration is a crown or a bridge framework.

4. The method according to claim 2, wherein said data of a contour of said dental restoration is derived from the captured position of a radiographic guide, which provides said virtually planned final outcome of said medical procedure.

5. The method according to claim 2, wherein said data of a contour of said dental restoration is derived from at least one virtual library tooth, which provides said virtually planned final outcome of said medical procedure.

6. A computer program enabling carrying out of the method according to claim 1.

7. The method according to claim 1, wherein said boundary surface is at least a contour of an existing jaw bone structure in said jaw bone.

8. The method according to claim 1, wherein said modification of a boundary surface comprises removal of an existing jaw bone structure.

9. The method according to claim 2, wherein said contour of said dental restoration is determined by surface matching techniques.

10. The method according to claim 9, wherein said surface matching technique is provided for determining an occlusion line.

11. The method according to claim 1, wherein said virtual planning comprises virtual planning of a dental implant, and wherein further production data is provided for at least one surgical template for drill and implant guided surgery.

12. The method according to claim 1, wherein said virtually planned medical procedure is a dental restorative procedure comprising dental surgery.

13. The method according to claim 1, wherein said virtual planning comprises virtual planning of a distraction procedure in relation to a previously virtually planned position of a dental restoration having said position data.

14. The method according to claim 13, wherein further production data is provided for at least a holder element devised for performing said distraction procedure.

15. A system for computer-implemented virtual planning of a medical procedure of a patient, which medical procedure comprises providing a patient configured bone structure in a jaw bone of said patient, said medical procedure comprising the removal or the distraction of an existing jaw bone structure; said system comprising
    a unit for generating production data based on said virtual planning, wherein said production data is configured for subsequent use in production of a cutting template, which is devised for use in said medical procedure, and devised for arrangement in said patient for facilitating said medical procedure by providing guidance when cutting a bone structure,
    wherein said system for virtual planning of the medical procedure comprises a graphical user interface for inputting to a software run on a medical workstation position data for a position of at least a part of a dental restoration in relation to said jaw bone, and
    a unit for virtual planning of a modification of a boundary surface at said jaw bone as a function of said position data, wherein said unit for virtual planning comprises a monitor configured to display a rendered visualization of said boundary surface, wherein said virtual planning comprises the planning of cutting a jaw bone structure, said planning generating the production data for use in the production of said cutting template.

16. A computer program for processing by a computer, the computer program comprising
    a first code segment for virtual planning of a medical procedure of a patient, which medical procedure comprises providing a patient configured bone structure in a jaw bone of said patient, said medical procedure comprising the removal or the distraction of an existing jaw bone structure;
    a second code segment for generating production data based on said virtual planning, wherein said production data is configured for subsequent use in production of a cutting template, which is devised for use in said medical procedure, and devised for arrangement in said patient for facilitating said medical procedure by providing guidance when cutting a jaw bone structure;
    a third code segment for providing position data for a position of at least a part of a dental restoration in relation to said jaw bone, and
    a fourth code segment for virtual planning of a modification of a boundary surface at said body portion as a function of said position data wherein said virtual planning comprises the planning of cutting a jaw bone structure, said planning generating the production data for use in the production of said cutting template.

17. A computer-readable medium having embodied thereon the computer program of claim 16.

* * * * *